(12) United States Patent
Schmitz et al.

(10) Patent No.: US 8,975,276 B2
(45) Date of Patent: Mar. 10, 2015

(54) INHIBITORS OF PDE10

(75) Inventors: William D. Schmitz, Cheshire, CT (US);
Mikkel V. DeBenedetto, Middletown,
CT (US); S. Roy Kimura, Stamford, CT
(US)

(73) Assignee: Bristol-Myers Squibb Company,
Princeton, NJ (US)

( * ) Notice: Subject to any disclaimer, the term of this
patent is extended or adjusted under 35
U.S.C. 154(b) by 345 days.

(21) Appl. No.: 13/531,840

(22) Filed: Jun. 25, 2012

(65) Prior Publication Data

US 2013/0165447 A1 Jun. 27, 2013

Related U.S. Application Data

(60) Provisional application No. 61/502,481, filed on Jun. 29, 2011.

(51) Int. Cl.
*C07D 471/04* (2006.01)
*C07D 471/14* (2006.01)
*C07D 519/00* (2006.01)
*C07D 487/04* (2006.01)

(52) U.S. Cl.
CPC ............ *C07D 519/00* (2013.01); *C07D 471/04* (2013.01); *C07D 471/14* (2013.01); *C07D 487/04* (2013.01)
USPC .......................................... 514/300; 546/121

(58) Field of Classification Search
None
See application file for complete search history.

(56) References Cited

U.S. PATENT DOCUMENTS

| 5,693,652 | A | 12/1997 | Takase et al. |
| 6,900,220 | B2 | 5/2005 | Becker et al. |
| 7,504,501 | B2 | 3/2009 | Wyvratt et al. |
| 2011/0065727 | A1 | 3/2011 | De Peretti |

FOREIGN PATENT DOCUMENTS

| WO | WO 02/066477 | 8/2002 |
| WO | WO 03/093499 | 11/2003 |
| WO | WO 2005/060571 | 7/2005 |
| WO | WO 2005/070180 | 8/2005 |
| WO | WO 2007/034282 | 3/2007 |
| WO | WO 2009/144392 A1 | 12/2009 |
| WO | WO 2010/065674 | 6/2010 |
| WO | WO 2010/114971 | 10/2010 |
| WO | WO 2011/036127 A1 | 3/2011 |
| WO | WO 2011/072695 | 6/2011 |
| WO | WO 2011/110545 | 9/2011 |

OTHER PUBLICATIONS

Partial International Search Report Oct. 22, 2012.
Ak-Tel, Taleb H. "Post Groebke-Blackburn multicomponent protocol: Synthesis of new polyfunctional imidazo[1,2-a]pyrimidine and imidazo[1,2-a]pyrimidine derivatives as potential antimicrobial agents," European Journal of Medicinal Chemistry, vol. 45, pp. 5848-5855 (2010).
Biftu, T. et al., "Synthesis and SAR studies of very potent imidazopyridine antiprotozoal agents," Bioorganic & Medicinal Chemistry Letters, vol. 16, pp. 2479-2483 (2006).
Fujishige, K., et al., "Cloning and Characterization of a Novel Human Phosphodiesterase That Hydrolyzes Both cAMP and cGMP (PDE10A)," The Journal of Biological Chemistry, vol. 274, No. 26, pp. 18438-18445 (1999).
Loughney, K. et al., "Isolation and characterization of PDE10A, a novel human 3', 5'-cyclic nucleotide phosphodiesterase," Gene, vol. 234, pp. 109-117 (1999).
Rodefer, J.S., et al., "PDE10A inhibition reverses subchronic PCP-induced deficits in attentional set-shifting in rats," European Journal of Neuroscience, vol. 21, pp. 1070-1076 (2005).
Scribner, A. et al., "Synthesis and biological activity of imidazopyridine anticoccidial agents: Part II," European Journal of Medicinal Chemistry, vol. 43, pp. 1123-1151 (2008).
Si, H., et al., "Predicting the activity of drugs for a group of imidazopyridine anticoccidial compounds," European Journal of Medicinal Chemistry, vol. 44, pp. 4044-4050 (2009).
Siuciak, J.A., et al., "Genetic deletion of the striatum-enriched phosphodiesterase PDE10A: Evidence for altered striatal function," Neuropharmacology, vol. 51, pp. 374-385 (2006).
Siuciak, J.A., et al., "Inhibition of the striatum-enriched phosphodiesterase PDE10A: A novel approach to the treatment of psychosis," Neuropharmacology, vol. 51, pp. 386-396 (2006).
Soderling, S.H., et al., "Isolation and characterization of a dual-substrate phosphodiesterase gene family: PDE10A," Proc. Natl. Acad. Sc. USA, vol. 96, pp. 7071-7076 (Jun. 1999).

*Primary Examiner* — Bong-Sook Baek
(74) *Attorney, Agent, or Firm* — Pamela A. Mingo; Gary D. Greenblatt

(57) ABSTRACT

PDE10 inhibitors having the general formula (I)

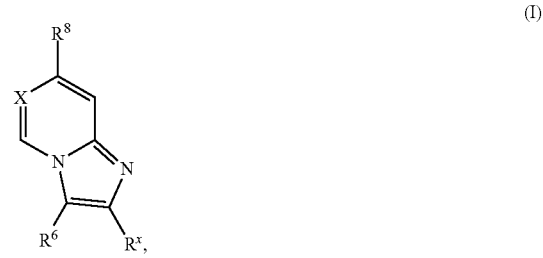

are disclosed. Compositions comprising the compounds and methods for using the compounds to inhibit PDE10 are also disclosed.

8 Claims, No Drawings

INHIBITORS OF PDE10

CROSS-REFERENCE TO RELATED APPLICATIONS

This application claims the benefit of U.S. Provisional Application Ser. No. 61/502,481 filed Jun. 29, 2011.

The present disclosure is generally directed to compounds which inhibit PDE10, compositions comprising such compounds, and methods for inhibiting the function of the PDE10.

Phosphodiesterases (PDEs) are intracellular enzymes that hydrolyze cyclic adenosine monophosphate (cAMP) and cyclic guanosine monophosphate (cGMP) to adenosine monophosphate (AMP) and guanosine monophosphate (GMP), respectively. cAMP and cGMP serve as secondary messengers in several cellular pathways. For example, cAMP and cGMP control activity of cAMP and cGMP-dependent kinases, as well as other proteins with cyclic nucleotide response elements, which in turn controls levels of phosphorylation of proteins that are involved in cellular signaling processes. In neurons, cAMP and cGMP levels impact key neuronal functions such as synaptic transmission, neuronal differentiation, and survival. PDEs are critical regulators of cellular processes because they hydrolyze cAMP and cGMP, thereby generating inactive monophosphates. Inhibitors of PDEs will result in increased levels of cAMP and/or cGMP, thereby enhancing levels of signaling.

To date, 11 PDE families have been identified based on their amino acid sequences, catalytic and regulatory characteristics, and sensitivity to small molecule inhibitors. Some PDEs utilize cAMP as a substrate, some hydrolyze cGMP, and some PDEs hydrolyze both cAMP and cGMP. Most PDEs have widespread expression while some are more tissue-specific. As a result of their distinct enzymatic activities and localization, PDEs (and subtypes within families) can serve distinct physiological functions. PDE10 was reported in 1999 (K. Fujishige et al, J. Biol. Chem. 1999, 274, pages 18438-18445; K. Loughney et al, Gene 1999, 234, pages 109-117; S. H. Soderling et al, Proc. Natl. Acad. Sci. USA 1999, 96, pages 7071-7076). PDE10 is a dual substrate PDE that hydrolyzes both cAMP and cGMP. The expression of PDE10 is highest in the brain, particularly in the medium spiny neurons (MSN) of the striatum. The striatal medium spiny neurons are the first input site of the basal ganglia circuit function. The tissue distribution of PDE10 indicates that PDE10 inhibitors can be used to raise levels of cAMP and/or cGMP within cells that express PDE10 in the brain. PDE10 has low levels of expression in the periphery suggesting a reduced propensity for peripheral side effects.

PDE10 KO animals exhibit an antipsychotic phenotype in multiple models thought to be predictive of antipsychotic activity. Additionally, multiple PDE10 inhibitors, that span multiple chemotypes, produce antipsychotic-like behavioral activity (for a review, see T. Chappie et al in Current Opinion in Drug Discovery & Development 2009, 12, pages 458-467). For example, the PDE10 inhibitor papaverine has been shown to be active in several antipsychotic models (WO 03/093499, J. A. Siuciak et al Neuropharmacology, 2006, 51, pages 386-396; J. A. Siuciak et al, Neuropharmacology 2006, 51, pages 374-385). PDE10 inhibitors also exhibit efficacy in models of cognition (for example, J. S. Rodefer et al, Eur. J. Neurosci., 2005, 21, pages 1070-1076). U.S. Pat. No. 5,693,652 discloses a method for treating certain neurologic and psychiatric disorders with the selective PDE10 inhibitor papaverine.

The localization of PDE10 in the brain suggests that PDE10 inhibitors would be useful in the treatment of psychiatric and neurological diseases. These diseases include but are not limited to schizophrenia; positive, negative, and/or cognitive symptoms associated with schizophrenia; delusional disorder; substance-induced psychotic disorder; anxiety disorders such as panic disorder, obsessive-compulsive disorder, acute stress disorder or generalized anxiety disorders; drug addiction; movement disorders such as Parkinson's disease, Huntington's disease or restless leg syndrome; cognition deficiency disorders such as Alzheimer's disease or multi-infarct dementia; mood disorders such as depression or bipolar disorders; or neuropsychiatric diseases such as psychosis, attention-deficit/hyperactivity disorder or related attentional disorders.

The compounds of the present disclosure are PDE10 inhibitors for the treatment of the above-mentioned psychiatric and neurological disorders.

In its first aspect the present disclosure provides a compound of formula (I)

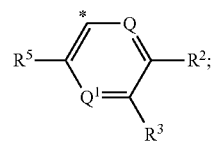

or a pharmaceutically acceptable salt thereof, wherein
$R^x$ is selected from $C_3$-$C_5$ cycloalkyl and

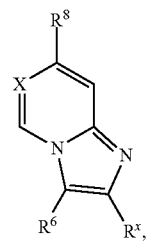

(I)

wherein * denotes the point of attachment to the parent molecule;
Q is selected from N and $CR^1$;
$Q^1$ is selected from N and $CR^4$;
$R^1$-$R^5$ are independently selected from hydrogen, $C_1$-$C_6$ alkoxy, $C_1$-$C_6$ alkyl, cyano, $C_3$-$C_5$ cycloalkyl, halo, and pyrrolidinyl;
$R^6$ is selected from hydrogen and $C_1$-$C_6$ alkyl;
X is selected from N and $CR^7$;
one of $R^7$ and $R^8$ is selected from hydrogen, cyano, halo, and pyrrolidinyl optionally substituted with one halogen; and the other is a heteroaromatic group of formula (II) containing from 2 to 4 nitrogen atoms:

(II)

wherein:
Y is N or CH; and
Z is N or C; and wherein the heteroaromatic group may be optionally substituted with one, two, or three substituents independently selected from $C_1$-$C_6$ alkoxy; $C_1$-$C_6$ alkyl; aryl; cyano; halo; halo($C_1$-$C_6$)alkyl; and $C_1$-$C_6$ hydroxyalkyl; and wherein * denotes the point of attachment to the parent molecule; provided that when X is N, $R^8$ is the heteroaromatic group of formula (II).

In a first embodiment of the first aspect the present disclosure provides a compound of formula (I), or a pharmaceutically acceptable salt thereof, wherein X is $CR^7$. In a second embodiment $R^7$ is selected from hydrogen, cyano, and halo and pyrrolidinyl optionally substituted with one halogen.

In a third embodiment of the first aspect the present disclosure provides a compound of formula (I), or a pharmaceutically acceptable salt thereof, wherein $R^8$ is

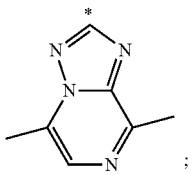

wherein * denotes the point of attachment to the cyclopropyl ring.

In a second aspect the present disclosure provides a compound of formula (II)

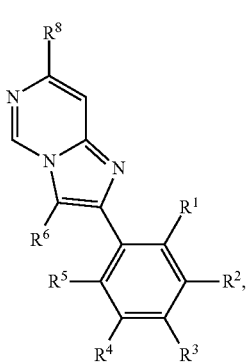

(II)

or a pharmaceutically acceptable salt thereof, wherein

X is selected from N and $CR^7$;

$R^1$-$R^5$ are independently selected from hydrogen, $C_1$-$C_6$ alkoxy, $C_1$-$C_6$ alkyl, cyano, and halo;

$R^6$ is selected from hydrogen and $C_1$-$C_6$ alkyl;

one of $R^7$ and $R^8$ is selected from hydrogen, cyano, and halo and the other is a heteroaromatic group of formula (II) containing from 2 to 4 nitrogen atoms:

(II)

wherein:

Y is N or CH; and

Z is N or C; and wherein the heteroaromatic group may be optionally substituted with one, two, or three substituents independently selected from $C_1$-$C_6$ alkoxy; $C_1$-$C_6$ alkyl; aryl; cyano; halo; halo($C_1$-$C_6$)alkyl; and $C_1$-$C_6$ hydroxyalkyl; and wherein * denotes the point of attachment to the parent molecule; provided that when X is N, $R^8$ is the heteroaromatic group of formula (II).

In a third aspect the present disclosure provides a composition comprising a compound of formula (I), or a pharmaceutically acceptable salt thereof, and a pharmaceutically acceptable carrier.

In a fourth aspect the present disclosure provides a method of treating a disorder selected from schizophrenia; positive, negative, and/or cognitive symptoms associated with schizophrenia; delusional disorder; substance-induced psychotic disorder; panic disorder; obsessive-compulsive disorder; acute stress disorder; generalized anxiety disorders; drug addiction; Parkinson's disease; Huntington's disease; restless leg syndrome; Alzheimer's disease; multi-infarct dementia; depression; bipolar disorders; psychosis, and attention-deficit/hyperactivity disorder in a patient, comprising administering to the patient a therapeutically effective amount of a compound of formula (I), or a pharmaceutically acceptable salt thereof. In a first embodiment of the fourth aspect, the disorder is schizophrenia.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

The term "$C_1$-$C_6$ alkoxy," as used herein, refers to a $C_1$-$C_6$ alkyl group attached to the parent molecular moiety through an oxygen atom.

The term "$C_1$-$C_6$ alkyl," as used herein, refers to a group derived from a straight or branched chain saturated hydrocarbon containing from one to six carbon atoms.

The term "aryl," as used herein, refers to a phenyl ring, optionally substituted with halogen, $C_1$-$C_6$ alkyl, $C_1$-$C_6$ alkoxy, or halo($C_1$-$C_6$)alkyl.

The term "cyano," as used herein, refers to —CN.

The terms "halo" and "halogen," as used herein, refer to F, Cl, Br, and I.

The term "halo($C_1$-$C_6$)alkyl," as used herein, refers to a $C_1$-$C_6$ alkyl group substituted with one, two, or three halogen atoms.

The term "hydroxy," as used herein, refers to —OH.

The term "$C_1$-$C_6$ hydroxyalkyl," as used herein, refers to a $C_1$-$C_6$ alkyl group substituted with one hydroxy group.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable basic functionality with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

The term "compounds of the disclosure", and equivalent expressions, are meant to embrace compounds of formula (I), and pharmaceutically acceptable enantiomers, diastereomers, and salts thereof. Similarly, references to intermediates, are meant to embrace their salts where the context so permits.

The term "patient" includes both human and other mammals.

The term "pharmaceutical composition" means a composition comprising a compound of the disclosure in combination with at least one additional pharmaceutical carrier, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Ingredients listed in Remington's Pharmaceutical Sciences, 18$^{th}$ ed., Mack Publishing Company, Easton, Pa. (1999) for example, may be used.

The phrase "pharmaceutically acceptable" is employed herein to refer to those compounds, materials, compositions, and/or dosage forms which are, within the scope of sound medical judgment, suitable for use in contact with the tissues of patients without excessive toxicity, irritation, allergic response, or other problem or complication commensurate with a reasonable risk/benefit ratio.

The term "therapeutically effective amount" means the total amount of each active component that is sufficient to show a meaningful patient benefit. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "treat" and "treating" refers to: (i) preventing a disease, disorder or condition from occurring in a patient which may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

Asymmetric centers exist in the compounds of the present disclosure. It should be understood that the disclosure encompasses all stereochemical forms, or mixtures thereof, which possess the ability to inhibit PDE10.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

Pharmaceutical formulations may be presented in unit dose forms containing a predetermined amount of active ingredient per unit dose. Dosage levels of between about 0.01 and about 150 milligram per kilogram ("mg/kg") body weight per day, preferably between about 0.05 and about 100 mg/kg body weight per day of the compounds of the disclosure are typical in a monotherapy for the prevention and treatment of the disorders described herein. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the disclosure and one or more additional therapeutic and/or prophylactic agent, both the compound and the additional agent can be present in a dose that is less than or equal to the dosage normally administered in a monotherapy regimen. The compositions of this disclosure may be co-formulated with one or more additional therapeutic or prophylactic agents, for example, in the form of a monolithic and/or bi/multi-layer tablet or may be administered separately from the therapeutic or prophylactic agent(s).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

This disclosure is intended to encompass compounds having formula (I) when prepared by synthetic processes or by metabolic processes including those occurring in the human or animal body (in vivo) or processes occurring in vitro.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The abbreviations used in the present application, including particularly in the illustrative schemes and examples which follow, are well-known to those skilled in the art. Some of the abbreviations used are as follows: BOC or Boc for tert-butoxycarbonyl; MeOH for methanol; min or mins for minutes; ACN for acetonitrile; TFA for trifluoroacetic acid; tBuOH for tert-butanol; DMSO for dimethylsulfoxide; DMF for N,N-dimethylformamide; HATU for 2-(7-aza-1H-benzotriazole-1-yl)-1,1,3,3-tetramethyluronium hexafluorophosphate; BINAP for 2,2'-bis(diphenylphosphino)-1,1'-binaphthyl; THF for tetrahydrofuran; EtOH for ethanol; and EtOAc for ethyl acetate.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

Synthetic Methods

Compounds of Formula I can be made according to methods known in the art and those illustrated in the schemes below. The schemes encompass reasonable variations known in the art. The variables describing general structural formulas and features in the synthetic schemes are distinct from and should not be confused with the variables in the claims or the rest of the specification. These variables are meant only to illustrate how to make some of the compounds of this invention.

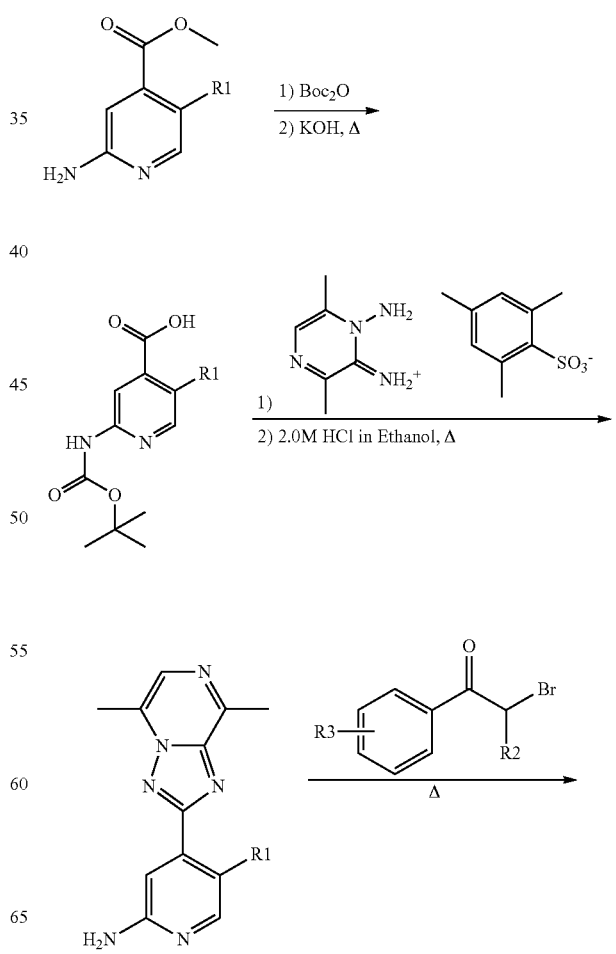

-continued

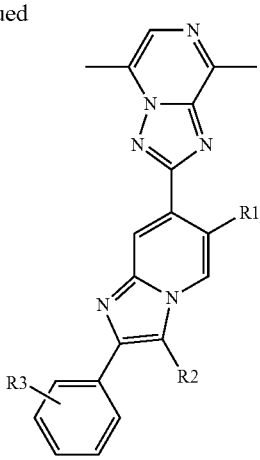

The following HPLC conditions were used in the preparing the compounds below.

LC/MS Method 1: Start % B=0 Final % B=100
Gradient Time=2 min Flow Rate=1 ml/min Wavelength=220
Solvent Pair=MeOH:Water:Ammonium Actetate
Solvent A=5% MeOH: 95% Water: 10 mM Ammonium Actetate
Solvent B=95% MeOH: 5% Water: 10 mM Ammonium Actetate
Column. Phenomenex LUNA C18, 30×2, 3 uM
LC/MS Method 2
Column=BEH C18 1.7 um (2.1×50 mm)
Start % B=2
Final % B=98
Gradient time=1.75 min
Stop time=2.20 min
Flow Rate=0.8 mL/min
Wavelength=220 nm
Solvent A=100% $H_2O$ w/0.05% TFA
Solvent B=100% ACN w/0.05% TFA HPLC Method 1:

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 methanol:water with 20-mM ammonium acetate; Gradient: 55-85% B over 30 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 40-60% B over 20 minutes, then a 4-minute hold at 100% B; Flow: 25 mL/min. Fractions containing the desired product were combined and dried via centrifugal evaporation. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

HPLC Method 2:

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 45-85% B over 20 minutes, then a 4-minute hold at 100% B; Flow: 20 mL/min. Fractions containing the desired product were combined and dried via centrifugal evaporation. The material was further purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 10-100% B over 20 minutes, then a 4-minute hold at 100% B; Flow: 25 mL/min. Fractions containing the desired product were combined and dried via centrifugal evaporation. The yield of the product was 0.8 mg, and its estimated purity by LCMS analysis was 97%. Two LCMS were used to determine purity. Injection 1: Column: Waters BEH C18, 2.0×50 mm, 1.7 μm; Mobile Phase A: 5:95 $ACN:H_2O$ with 10 mM $NH_4OAc$; Mobile Phase B: 95:5 $ACN:H_2O$ with 10 mM $NH_4OAc$; Temperature: 40° C.; Gradient: 0.5 min hold at 0% B, 0-100% B over 4 min, then a 0.5 min hold at 100% B; Flow: 1 mL/min. Injection 2: Column: Waters BEH C18, 2.0×50 mm, 1.7-μm; Mobile Phase A: 5:95 $MeOH:H_2O$ with 10 mM $NH_4OAc$; Mobile Phase B: 95:5 $MeOH:H_2O$ with 10 mM $NH_4OAc$; Temperature: 40° C.; Gradient 0.5 min hold at 0% B, 0-100% B over 4 min, then a 0.5-min hold at 100% B; Flow: 0.5 mL/min.

HPLC Method 3:

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 60-100% B over 12 minutes, then a 5-minute hold at 100% B; Flow: 20 mL/min. Fractions containing the desired product were combined and dried via centrifugal evaporation. The yield of the product was 1.3 mg, and its estimated purity by LCMS analysis was 100%. Two analytical LC/MS injections were used to determine the final purity. Injection 1 conditions: Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm particles; Mobile Phase A: 5:95 methanol:water with 10 mM ammonium acetate; mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

HPLC Method 4:

The crude material was purified via preparative LC/MS with the following conditions: Column: Waters XBridge C18, 19×200 mm, 5-μm particles; Guard Column: Waters XBridge C18, 19×10 mm, 5-μm particles; Mobile Phase A: water with 20-mM ammonium acetate; Mobile Phase B: 95:5 acetonitrile:water with 20-mM ammonium acetate; Gradient: 50-90% B over 12 minutes, then a 5-minute hold at 100% B; Flow: 20 mL/min. Fractions containing the desired product were combined and dried via centrifugal evaporation. The yield of the product was 2.6 mg, and its estimated purity by LCMS analysis was 94%. Two LCMS were used to determine purity. Injection 1: Column: Waters BEH C18, 2.0×50 mm, 1.7 µm; Mobile Phase A: 5:95 ACN:H$_2$O with 10 mM NH$_4$OAc; Mobile Phase B: 95:5 ACN:H$_2$O with 10 mM NH$_4$OAc; Temperature: 40° C.; Gradient 0.5 min hold at 0% B, 0-100% B over 4 min, then a 0.5 min hold at 100% B; Flow: 1 mL/min. Injection 2: Column: Waters BEH C18, 2.0×50 mm, 1.7-µm; Mobile Phase A: 5:95 MeOH:H$_2$O with 10 mM NH$_4$OAc; Mobile Phase B: 95:5 MeOH:H$_2$O with 10 mM NH$_4$OAc; Temperature: 40° C.; Gradient: 0.5 min hold at 0% B, 0-100% B over 4 min, then a 0.5-min hold at 100% B; Flow: 0.5 mL/min.

HPLC Method 5:

The crude material was purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 50-90% B over 12 minutes, then a 5-minute hold at 100% B; Flow: 20 mL/min. Fractions containing the desired product were combined and dried via centrifugal evaporation. The yield of the product was 4.6 mg, and its estimated purity by LCMS analysis was 100%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-µm particles; Mobile Phase A: 5:95 methanol:water with 10 mM ammonium acetate; mobile phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

HPLC Method 6:

The crude material was purified via preparative LC/MS with the following conditions: Column: Waters XBridge C18, 19×200 mm, 5-µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 40-80% B over 12 minutes, then a 5-minute hold at 100% B; Flow: 20 mL/min. Fractions containing the desired product were combined and dried via centrifugal evaporation. The yield of the product was 3.3 mg, and its estimated purity by LCMS analysis was 99%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

HPLC Method 7:

The crude material was purified via preparative LC/MS with the following conditions: Column: Waters XBridge C18, 19×200 mm, 5-1 µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 45-85% B over 12 minutes, then a 5-minute hold at 100% B; Flow: 20 mL/min. Fractions containing the desired product were combined and dried via centrifugal evaporation. The yield of the product was 3.2 mg, and its estimated purity by LCMS analysis was 90%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

HPLC Method 8:

The crude material was purified via preparative LC/MS with the following conditions: Column: Waters XBridge C18, 19×200 mm, 5-1 µm particles; Guard Column: Waters XBridge C18, 19×10 mm, 5-µm particles; Mobile Phase A: water with 20-mM ammonium acetate; Mobile Phase B: 95:5 acetonitrile:water with 20-mM ammonium acetate; Gradient: 50-90% B over 12 minutes, then a 5-minute hold at 100% B; Flow: 20 mL/min. Fractions containing the desired product were combined and dried via centrifugal evaporation. The yield of the product was 3.8 mg, and its estimated purity by LCMS analysis was 100%. Two analytical LC/MS injections were used to determine the final purity. Injection 1 conditions: Column: Waters BEH C18, 2.0×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-µm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

HPLC Method 9:

The crude material was purified via preparative LC/MS with the following conditions: Column: Waters XBridge C18, 30×100 mm, 5-µm particles; Guard Column: Waters XBridge C18, 19×10 mm, 5-µm particles; Mobile Phase A: 90:10 water:acetonitrile with 0.1% trifluoroacetic acid; Mobile Phase B: 90:10 acetonitrile:water with 0.1% trifluoroacetic acid; Gradient: 0% B over 2 minutes, then 20-70% B over 10 minutes; Flow: 42 mL/min. Fractions containing the desired product were combined and dried via centrifugal evaporation. The TFA salt was filtered through a 1 g/12 mL Giga Tube Strata-X-C 33u Polymeric Strong Cation using 25 mL of methanol. The product was eluted with 25 mL 2.0M ammonia in methanol. Two analytical LC/MS injections were used to determine the final purity using orthagonial column setup. Injection 1 conditions: Column 1: Sunfire C18, 3.0×150 mm, 3.5-µm particle; Column 2: Xbrdige Phenyl, 3.0×150 mm, 3.5-µm particle. Mobile Phase A: 5:95 acetonitrile:water with 0.1% TFA; Mobile Phase B: 95:5 acetonitrile:water with 0.1% TFA; Temperature: 40° C.; Gradient: 0-100% B over 15 minutes, then 3 minute hold at 100% B; Flow: 1 mL/min. Injection 2 conditions Column 1: Xbridge C18, 3.0×150 mm, 3.5-µm particle; Column 2: Xbrdige Phenyl, 3.0×150 mm, 3.5-µm particle. Mobile Phase A: 5:95 methanol:water with 10 mM ammonium bicarbonate; Mobile Phase B: 95:5 methanol:water with 10 mM ammonium bicarbonate; Temperature: 40° C.; Gradient: 0-100% B over 15 minutes, then 3 minute hold at 100% B; Flow: 1 mL/min.

HPLC Method 10:

The crude material was purified via preparative LC/MS with the following conditions: Column: Waters XBridge C18, 30×100 mm, 5-µm particles; Guard Column: Waters XBridge C18, 19×10 mm, 5-µm particles; Mobile Phase A: 90:10 water:acetonitrile with 0.1% trifluoroacetic acid; Mobile Phase B: 90:10 acetonitrile:water with 0.1% trifluoroacetic acid; Gradient: 0% B over 2 minutes, then 20-80% B over 15 minutes; Flow: 42 mL/min. Fractions containing the desired product were combined and dried via centrifugal evaporation. The TFA salt was filtered through a 1 g/12 mL Giga Tube Strata-X-C 33u Polymeric Strong Cation using 25 mL of methanol. The product was eluted with 25 mL 2.0M ammonia in methanol. Two analytical LC/MS injections were used to determine the final purity using orthagonial column setup. Injection 1 conditions: Column 1: Sunfire C18, 3.0×150 mm, 3.5-µm particle; Column 2: Xbrdige Phenyl, 3.0×150 mm, 3.5-µm particle. Mobile Phase A: 5:95 acetonitrile:water with 0.1% TFA; Mobile Phase B: 95:5 acetonitrile:water with 0.1% TFA; Temperature: 40° C.; Gradient: 0-100% B over 15 minutes, then 3 minute hold at 100% B; Flow: 1 mL/min. Injection 2 conditions Column 1: Xbridge C18, 3.0×150 mm, 3.5-µm particle; Column 2: Xbrdige Phenyl, 3.0×150 mm, 3.5-µm particle. Mobile Phase A: 5:95 methanol:water with 10 mM ammonium bicarbonate; Mobile Phase B: 95:5 methanol:water with 10 mM ammonium bicarbonate; Temperature: 40° C.; Gradient: 0-100% B over 15 minutes, then 3 minute hold at 100% B; Flow: 1 mL/min.

HPLC Method 11:

The crude material was purified via preparative LC/MS with the following conditions: Column: Waters XBridge C18, 30×100 mm, 5-µm particles; Guard Column: Waters XBridge C18, 19×10 mm, 5-µm particles; Mobile Phase A: 5:95 acetonitrile:water with 10 mM ammonium acetate; Mobile Phase B: 95:5 acetonitrile:water with 10 mM ammonium acetate; Gradient: 0% B over 2 minutes, then 0-100% B over 12 minutes; Flow: 42 mL/min. Fractions containing the desired product were combined and dried via centrifugal evaporation. Two analytical LC/MS injections were used to determine the final purity using orthagonial column setup. Injection 1 conditions: Column 1: Sunfire C18, 3.0×150 mm, 3.5-µm particle; Column 2: Xbrdige Phenyl, 3.0×150 mm, 3.5-µm particle. Mobile Phase A: 5:95 acetonitrile:water with 0.1% TFA; Mobile Phase B: 95:5 acetonitrile:water with 0.1% TFA; Temperature: 40° C.; Gradient: 0-100% B over 15 minutes, then 3 minute hold at 100% B; Flow: 1 mL/min. Injection 2 conditions Column 1: Xbridge C18, 3.0×150 mm, 3.5-µm particle; Column 2: Xbrdige Phenyl, 3.0×150 mm, 3.5-µm particle. Mobile Phase A: 5:95 methanol:water with 10 mM ammonium bicarbonate; Mobile Phase B: 95:5 methanol:water with 10 mM ammonium bicarbonate; Temperature: 40° C.; Gradient: 0-100% B over 15 minutes, then 3 minute hold at 100% B; Flow: 1 mL/min.

HPLC Method 12:

The crude material was purified via preparative LC/MS with the following conditions: Column: Waters XBridge C18, 30×100 mm, 5-µm particles; Guard Column: Waters XBridge C18, 19×10 mm, 5-µm particles; Mobile Phase A: 90:10 water:acetonitrile with 0.1% trifluoroacetic acid; Mobile Phase B: 90:10 acetonitrile:water with 0.1% trifluoroacetic acid; Gradient: 0% B over 2 minutes, then 0-60% B over 12 minutes; Flow: 42 mL/min. Fractions containing the desired product were combined and dried via centrifugal evaporation. The TFA salt was filtered through a 1 g/12 mL Giga Tube Strata-X-C 33u Polymeric Strong Cation using 25 mL of methanol. The product was eluted with 25 mL 2.0M ammonia in methanol. Two analytical LC/MS injections were used to determine the final purity using orthagonial column setup. Injection 1 conditions: Column 1: Sunfire C18, 3.0×150 mm, 3.5-µm particle; Column 2: Xbrdige Phenyl, 3.0×150 mm, 3.5-µm particle. Mobile Phase A: 5:95 acetonitrile:water with 0.1% TFA; Mobile Phase B: 95:5 acetonitrile:water with 0.1% TFA; Temperature: 40° C.; Gradient: 0-100% B over 15 minutes, then 3 minute hold at 100% B; Flow: 1 mL/min. Injection 2 conditions Column 1: Xbridge C18, 3.0×150 mm, 3.5-µm particle; Column 2: Xbrdige Phenyl, 3.0×150 mm, 3.5-µm particle. Mobile Phase A: 5:95 methanol:water with 10 mM ammonium bicarbonate; Mobile Phase B: 95:5 methanol:water with 10 mM ammonium bicarbonate; Temperature: 40° C.; Gradient: 0-100% B over 15 minutes, then 3 minute hold at 100% B; Flow: 1 mL/min.

INTERMEDIATE 1

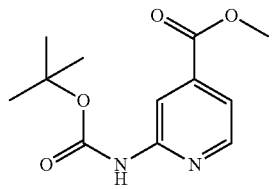 [SMILES: COC(=O)c1ccnc(NC(=O)OC(C)(C)C)c1]

methyl 2-((tert-butoxycarbonyl)amino)isonicotinate

A 500 mL round bottomed flask was charged with methyl 2-aminoisonicotinate (5.0 g, 32.9 mmol) and suspended in t-BuOH (200 mL). To this stirring solution was added di-tert-butyl dicarbonate (7.53 g, 34.5 mmol). The flask was vented and placed in an oil bath preheated to 50° C. The reaction mixture was let stir overnight. After 22 hours LCMS showed near complete conversion of starting material. The mixture was cooled to room temperature and filtered to yield 5.93 g of white solid. The material was taken on without any further purification. $^1$H NMR (400 MHz, DMSO-d$_6$) δ ppm 10.14 (1H, s), 8.43 (1H, dd, J=5.02, 0.75 Hz), 8.33 (1H, s), 7.45 (1H, dd, J=5.02, 1.51 Hz), 3.89 (3H, s), 1.48 (9H, s).

INTERMEDIATE 2

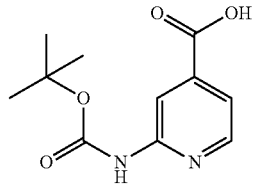 [SMILES: CC(C)(C)OC(=O)Nc1cc(C(=O)O)ccn1]

2-((tert-butoxycarbonyl)amino)isonicotinic acid, HCl

A 500 mL round bottomed flask was charged with methyl 2-((tert-butoxycarbonyl)amino)isonicotinate (5.95 g, 23.6 mmol) and suspended in methanol (118 ml). To this stirring solution was added 3.0M potassium hydroxide (23.6 mL, 70.8 mmol). The flask was vented and heated to 50° C. for 10 minutes. LCMS analysis showed clean and complete conversion of starting material to a single product consistent with the desired product by mass (m/z=237 [M−H]−). The mixture was cooled to room temperature and then 1.0N HCl was added to give a white precipitate. The solid was collected by filtration and dried overnight to give 2-((tert-butoxycarbonyl)amino)isonicotinic acid, HCl (5.2 g, 18.93 mmol, 80% yield). $^1$H NMR (400 MHz, DMSO-$d_6$) δ ppm 13.64 (1H, br. s.), 10.06 (1H, s), 8.39 (1H, d, J=5.27 Hz), 8.30 (1H, s), 7.42 (1H, dd, J=5.02, 1.51 Hz), 1.48 (9H, s).

INTERMEDIATE 3

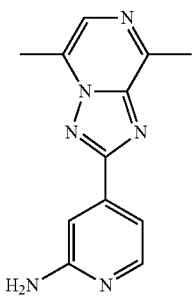

4-(5,8-dimethyl-1,2,41-triazolo[1,5-a]pyrazin-2-YL) pyridin-2-amine, 2 HCl

A 100 mL round bottomed flask was charged with 2-((tert-butoxycarbonyl)amino)isonicotinic acid, HCl (500 mg, 1.82 mmol) and dissolved in DMF (18.2 mL). To that stirring solution was added Hunig's Base (1.59 mL, 9.10 mmol) followed by HATU (900 mg, 2.37 mmol). After a few minutes, 1-amino-3,6-dimethylpyrazin-2(1H)-iminium 2,4,6-trimethylbenzenesulfonate (647 mg, 1.91 mmol) was added in one portion. The vial was sealed and let stir at room temperature. After 30 minutes, LCMS showed a large peak with the desired amide intermediate mass (m/z=357/359 [M−H]−/[M+H]+]. The reaction mixture was diluted with water and DCM and the aqueous was extract with DCM (×2) and discarded. The combined organics were washed with water (×1), saturated sodium bicarbonate (×1), and brine (×1), then dried over magnesium sulfate. The crude mixture was filtered then concentrated in a 40 mL pressure rated scintillation vial. The crude material was diluted with 2.5M HCl in ethanol (18.2 mL) and placed in a reaction block preheated to 65° C. and let stir overnight. After heating for 17 hours, LCMS showed >95% conversion of the uncyclized amide intermediate to desired triazolopyrazine. The mixture was cooled to room temperature and the white solid was collected by filtration as a 2-HCl salt. $^1$H NMR (400 MHz, DMSO-$d_6$) δ ppm 8.42 (2H, br. s.), 8.10-8.19 (2H, m), 7.90 (1H, d, J=1.00 Hz), 7.57 (1H, dd, J=6.65, 1.63 Hz), 2.85 (3H, s), 2.75 (3H, s). Mass found 241 [M+H]+.

EXAMPLE 1

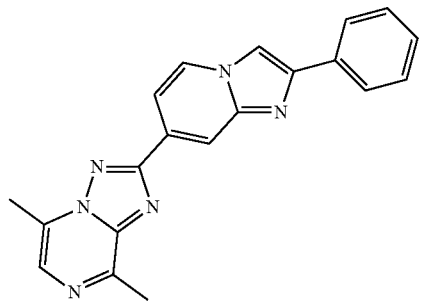 [SMILES: Cc1ncc(C)n2nc(-c3ccn4cc(-c5ccccc5)nc4c3)nc12]

5,8-dimethyl-2-(2-phenylimidazo[1,2-a]pyridin-7-yl)-[1,2,4]triazolo[1,5-a]pyrazine A 2-dram pressure rated vial was charged with 4-(5,8-dimethyl-[1,2,4]triazolo[1,5-a]pyrazin-2-yl)pyridin-2-amine, 2 HCl (20 mg, 0.064 mmol) and suspended in acetonitrile (639 p. 1). To that stirring solution was added potassium carbonate (44.1 mg, 0.319 mmol) followed by 2-bromo-1-phenylethanone (15.2 mg, 0.077 mmol). The vial was sealed and placed in a reaction block preheated to 100° C. The reaction was let stir overnight. After heating overnight, LCMS showed clean and complete conversion of the starting material to a major peak with the desired mass (m/z=341 [M+H]−). The mixture was cooled to room temperature and concentrated under reduced pressure. The crude material was purified by HPLC Method 1. $^1$H NMR (400 MHz, DMSO-$d_6$) δ ppm 8.84 (1H, d, J=7.03 Hz), 8.72 (1H, s), 8.43 (1H, s), 8.10 (1H, d, J=1.00 Hz), 7.97-8.02 (2H, m), 7.94 (1H, d, J=7.28 Hz), 7.52-7.59 (2H, m), 7.42-7.49 (1H, m), 2.86 (3H, s), 2.77 (3H, s). Mass found 341 [M+H]+.

EXAMPLE 2

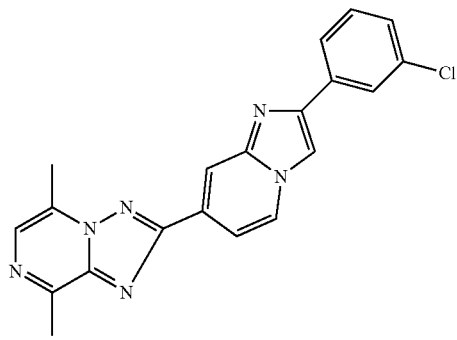 [SMILES: Cc1ncc(C)n2nc(-c3ccn4cc(-c5cccc(Cl)c5)nc4c3)nc12]

2-(2-(3-chlorophenyl)imidazo[1,2-a]pyridin-7-yl)-5,8-dimethyl-[1,2,4]triazolo[1,5-a]pyrazine Example 2 was prepared from 2-bromo-1-(3-chlorophenyl)ethanone following the experimental conditions described in the synthesis of Example 1. The crude material was purified by HPLC Method 11. ¹H NMR (400 MHz, MeOD) δ ppm 7.69 (1H, dd, J=7.03, 0.75 Hz), 7.55 (1H, s), 7.46 (1H, s), 7.06-7.11 (2H, m), 6.93-7.01 (2H, m), 6.54-6.60 (1H, m), 6.47-6.52 (1H, m), 2.08 (3H, s), 1.97 (3H, s). Mass found 375 [M+H]+.

EXAMPLE 3

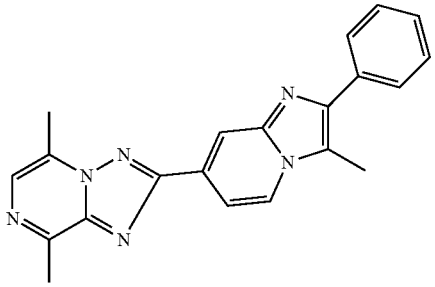 [SMILES: Cc1ncc(C)n2nc(-c3ccn4c(C)c(-c5ccccc5)nc4c3)nc12]

5,8-dimethyl-2-(3-methyl-2-phenylimidazo[1,2-a]pyridin-7-yl)-[1,2,4]triazolo[1,5-a]pyrazine Example 3 was prepared from 2-bromo-1-phenylpropan-1-one following the experimental conditions described in the synthesis of Example 1. The crude material was purified by HPLC Method 12. ¹H NMR (400 MHz, DMSO-d₆) δ ppm 8.55 (1H, d, J=7.28 Hz), 8.40 (1H, s), 8.08 (1H, s), 7.87 (2H, d, J=7.03 Hz), 7.78 (1H, dd, J=7.15, 1.63 Hz), 7.53 (2H, t, J=7.53 Hz), 7.37-7.46 (1H, m), 2.87 (3H, s), 2.79 (3H, s), 2.74 (3H, s). Mass found 355 [M+H]+.

EXAMPLE 4

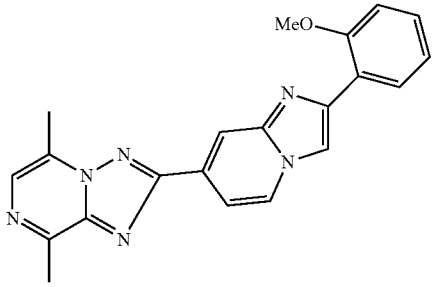 [SMILES: COc1ccccc1-c1cn2ccc(-c3nc4c(C)ncc(C)n4n3)cc2n1]

2-(2-(2-methoxyphenyl)imidazo[1,2-a]pyridin-7-yl)-5,8-dimethyl-[1,2,4]triazolo[1,5-a]pyrazine Example 4 was prepared from 2-bromo-1-(2-methoxyphenyl)ethanone following the experimental conditions described in the synthesis of Example 1. The crude material was purified by HPLC Method 2. ¹H NMR (500 MHz, DMSO-d₆) δ ppm 8.76 (1H, dd, J=7.02, 0.92 Hz), 8.57 (1H, d, J=0.61 Hz), 8.34-8.38 (2H, m), 8.08 (1H, d, J=0.92 Hz), 7.71 (1H, dd, J=7.02, 1.53 Hz), 7.35-7.40 (1H, m), 7.18 (1H, d, J=7.63 Hz), 7.11 (1H, td, J=7.48, 0.92 Hz), 4.01 (3H, s), 2.87 (3H, s), 2.78 (3H, s). Mass found 370 [M+H]+.

EXAMPLE 5

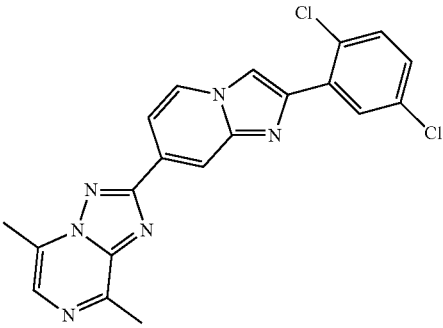 [SMILES: Cc1ncc(C)n2nc(-c3ccn4cc(-c5cc(Cl)ccc5Cl)nc4c3)nc12]

2-(2-(2,5-dichlorophenyl)imidazo[1,2-a]pyridin-7-yl)-5,8-dimethyl-[1,2,4]triazolo[1,5-a]pyrazine Example 5 was prepared from 2-bromo-1-(2,5-dichlorophenyl)ethanone following the experimental conditions described in the synthesis of Example 1. The crude material was purified by HPLC Method 3. ¹H NMR (500 MHz, DMSO-d₆) δ ppm 8.87 (1H, d, J=0.92 Hz), 8.82 (1H, dd, J=7.02, 0.92 Hz), 8.41-8.44 (1H, m), 8.34 (1H, d, J=2.75 Hz), 8.09 (1H, d, J=0.92 Hz), 7.79 (1H, dd, J=7.02, 1.83 Hz), 7.66 (1H, d, J=8.54 Hz), 7.49 (1H, dd, J=8.54, 2.75 Hz), 2.87 (3H, s), 2.78 (3H, s). Mass found 410 [M+H]+.

EXAMPLE 6

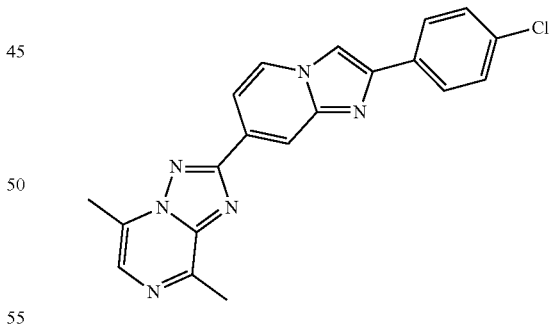

2-(2-(4-chlorophenyl)imidazo[1,2-a]pyridin-7-yl)-5,8-dimethyl-[1,2,4]triazolo[1,5-a]pyrazine Example 6 was prepared from 2-bromo-1-(4-chlorophenyl)ethanone following the experimental conditions described in the synthesis of Example 1. The crude material was purified by HPLC Method 4. ¹H NMR (500 MHz, DMSO-d₆) δ ppm 8.67-8.72 (1H, m), 8.59 (1H, s), 8.34 (1H, s), 8.01-8.07 (3H, m), 7.72 (1H, dd, J=7.02, 1.53 Hz), 7.52-7.56 (2H, m), 2.86 (3H, s), 2.76 (3H, s). Mass found 375 [M+H]+.

EXAMPLE 7

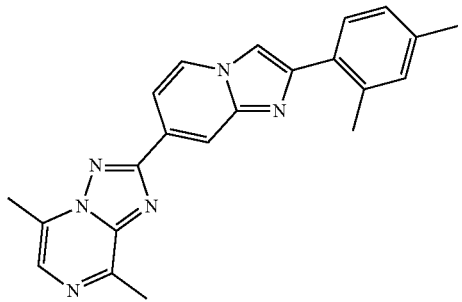

2-(2-(2,4-dimethylphenyl)imidazo[1,2-a]pyridin-7-yl)-5,8-dimethyl-[1,2,4]triazolo[1,5-a]pyrazine Example 7 was prepared from 2-bromo-1-(2,5-dimethylphenyl)ethanone following the experimental conditions described in the synthesis of Example 1. The crude material was purified by HPLC Method 5. $^1$H NMR (500 MHz, DMSO-$d_6$) δ ppm 8.72 (1H, dd, J=7.02, 0.92 Hz), 8.36-8.39 (1H, m), 8.34 (1H, s), 8.07 (1H, d, J=0.92 Hz), 7.87 (1H, d, J=7.63 Hz), 7.73 (1H, dd, J=7.02, 1.53 Hz), 7.12-7.16 (2H, m), 2.87 (3H, d, J=0.61 Hz), 2.78 (3H, s), 2.56 (3H, s), 2.34 (3H, s). Mass found 369 [M+H]+.

EXAMPLE 8

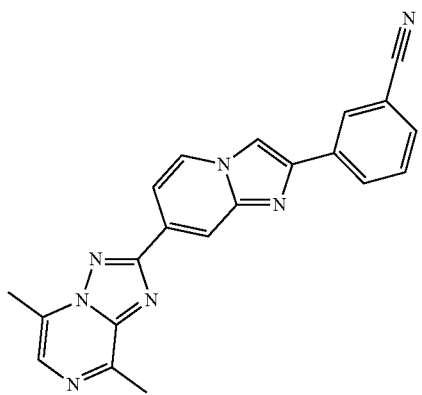 [SMILES: Cc1ncc(C)n2nc(-c3ccn4cc(-c5cccc(C#N)c5)nc4c3)nc12]

3-(7-(5,8-dimethyl-[1,2,4]triazolo[1,5-a]pyrazin-2-yl)imidazo[1,2-a]pyridin-2-yl)benzonitrile Example 8 was prepared from 3-(2-bromoacetyl)benzonitrile following the experimental conditions described in the synthesis of Example 1. The crude material was purified by HPLC Method 6. $^1$H NMR (500 MHz, DMSO-$d_6$) δ ppm 8.76 (1H, dd, J=7.02, 0.92 Hz), 8.74 (1H, s), 8.46 (1H, t, J=1.68 Hz), 8.41 (1H, s), 8.38 (1H, s), 8.09 (1H, d, J=0.92 Hz), 7.83-7.86 (1H, m), 7.77 (1H, dd, J=7.02, 1.83 Hz), 7.72 (1H, t, J=7.78 Hz), 2.87 (3H, s), 2.78 (3H, s). Mass found 366 [M+H]+.

EXAMPLE 9

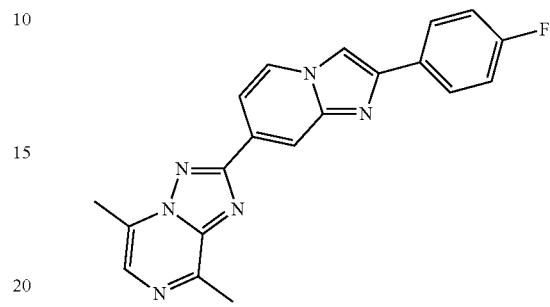

2-(2-(4-fluorophenyl)imidazo[1,2-a]pyridin-7-yl)-5,8-dimethyl-[1,2,4]triazolo[1,5-a]pyrazine Example 9 was prepared from 2-bromo-1-(4-fluorophenyl)ethanone following the experimental conditions described in the synthesis of Example 1. The crude material was purified by HPLC Method 7. $^1$H NMR (500 MHz, DMSO-$d_6$) δ ppm 8.70 (1H, dd, J=7.02, 0.92 Hz), 8.55 (1H, s), 8.34-8.38 (1H, m), 8.04-8.09 (3H, m), 7.72 (1H, dd, J=7.02, 1.83 Hz), 7.29-7.35 (2H, m), 2.86 (3H, d, J=0.61 Hz), 2.77 (3H, s). Mass found 359 [M+H]+.

EXAMPLE 10

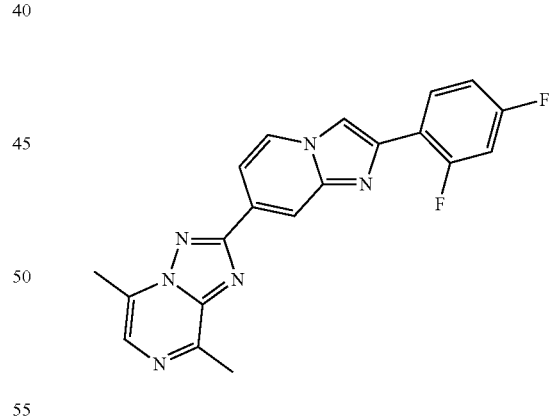

2-(2-(2,4-difluorophenyl)imidazo[1,2-a]pyridin-7-yl)-5,8-dimethyl-[1,2,4]triazolo[1,5-a]pyrazine Example 10 was prepared from 2-bromo-1-(2,4-difluorophenyl)ethanone following the experimental conditions described in the synthesis of Example 1. The crude material was purified by HPLC Method 8. $^1$H NMR (500 MHz, DMSO-$d_6$) δ ppm 8.78 (1H, dd, J=7.32, 0.92 Hz), 8.49 (1H, d, J=4.27 Hz), 8.39 (1H, s), 8.35 (1H, td, J=8.70, 7.02 Hz), 8.08 (1H, d, J=0.92 Hz), 7.75 (1H, dd, J=7.02, 1.53 Hz), 7.43

(1H, ddd, J=11.60, 9.16, 2.44 Hz), 7.27 (1H, td, J=8.39, 2.75 Hz), 2.87 (3H, s), 2.78 (3H, s). Mass found 377 [M+H]+.

INTERMEDIATE 4

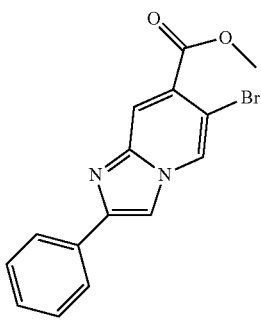 [SMILES: COC(=O)c1cc2nc(-c3ccccc3)cn2cc1Br]

methyl 6-bromo-2-phenylimidazo[1,2-a]pyridine-7-carboxylate

A 40 mL pressure rated scintillation vial was charged with methyl 2-amino-5-bromoisonicotinate (500 mg, 2.16 mmol) and 2-bromo-1-phenylethanone (474 mg, 2.38 mmol). The mixture was partially dissolved in ethanol (10.8 mL) and the reaction vessel was placed in a reaction block preheated to 100° C. The reaction mixture was let stir overnight. After heating for 18 hours, LCMS showed complete conversion of the starting material to a major peak with the desired mass (m/z=332 [M+H]+). The mixture was allowed to come to ambient temperature. After several hours a red precipitate had formed and was filtered. The solid was dried in open air overnight. Methyl 6-bromo-2-phenylimidazo[1,2-a]pyridine-7-carboxylate (400 mg, 1.208 mmol, 55.8% yield) was collected as a red solid. $^1$H NMR (400 MHz, DMSO-$d_6$) δ ppm 9.12 (1H, s), 8.58 (1H, s), 8.18 (1H, s), 8.01 (2H, dd, J=8.28, 1.25 Hz), 7.53 (2H, t, J=7.53 Hz), 7.41-7.47 (1H, m), 3.93 (3H, s). Mass found 332 [M+H]+.

INTERMEDIATE 5

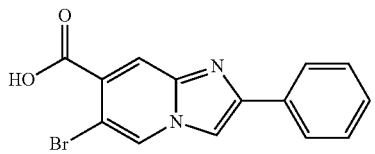 [SMILES: O=C(O)c1cc2nc(-c3ccccc3)cn2cc1Br]

6-bromo-2-phenylimidazo[1,2-a]pyridine-7-carboxylic acid

A 50 mL round bottomed flask was charged with methyl 6-bromo-2-phenylimidazo[1,2-a]pyridine-7-carboxylate (400 mg, 1.21 mmol) and suspended in methanol (12.1 mL). To that stirring solution was added 3.0M potassium hydroxide (0.805 mL, 2.42 mmol). The flask was fitted with a reflux condenser and placed in an oil bath preheated to 70° C. After 2.5 hours, LCMS showed clean and complete conversion of the starting material to a major peak with the desired mass (m/z=318 [M+H]+). The mixture was cooled to room temperature and 1.0N HCl was added. The reaction mixture was cooled in an ice bath and a pink solid formed. After 30 minutes, the solids were filtered and dried under high vacuum overnight. 6-Bromo-2-phenylimidazo[1,2-a]pyridine-7-carboxylic acid (283 mg, 0.892 mmol, 73.9% yield) was recovered as a pink solid. $^1$H NMR (400 MHz, DMSO-$d_6$) ppm 9.04 (1H, s), 8.51 (1H, s), 8.09 (1H, s), 7.96-8.03 (2H, m), 7.45-7.54 (2H, m), 7.35-7.43 (1H, m) Mass found 318 [M+H]+.

EXAMPLE 11

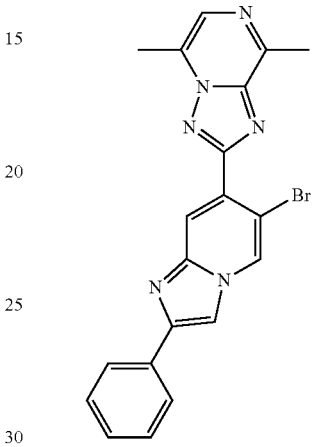

2-(6-bromo-2-phenylimidazo[1,2-a]pyridin-7-yl)-5,8-dimethyl-[1,2,4]-triazolo[1,5-a]pyrazine Example 11 was prepared from 6-bromo-2-phenylimidazo[1,2-a]pyridine-7-carboxylic acid following the experimental conditions described in the synthesis of Intermediate 3. The crude material was purified by HPLC Method 9. $^1$H NMR (400 MHz, DMSO-$d_6$) δ ppm 9.15 (1H, s), 8.52 (1H, s), 8.19 (1H, s), 8.13 (1H, s), 8.04 (2H, d, J=7.03 Hz), 7.46-7.54 (2H, m), 7.36-7.43 (1H, m), 2.87 (3H, s), 2.77 (3H, s). Mass found 377 [M+H]+.

EXAMPLE 12

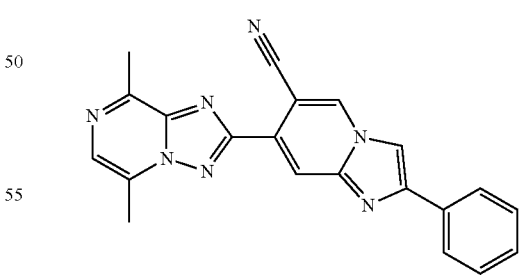

7-(5,8-dimethyl-[1,2,4]triazolo[1,5-a]pyrazin-2-yl)-2-phenylimidazo[1,2-a]pyridine-6-carbonitrile A 2-dram pressure rated scintillation vial was charged with 2-(6-bromo-2-phenylimidazo[1,2-a]pyridin-7-yl)-5,8-dimethyl-[1,2,4]triazolo[1,5-a]pyrazine (20 mg, 0.048 mmol) and suspended in DMF (477 mL). To that stirring solution was added zinc cyanide (5.60 mg, 0.048 mmol). The vial was sealed and degassed using dry argon and sonication for 1 minute. Tetrakis(triphenylphosphine)palladium(0) (16.5 mg, 0.014 mmol) was then added in one portion. The vial was resealed, flushed with argon, and placed in a reaction block preheated to 90° C. After 1.25 hours, LCMS showed complete conversion of starting material to a major peak with the desired product (m/z=366 [M+H]+). Upon cooling, a solid began to form. The crude material was purified by HPLC method 10. $^1$H NMR (400 MHz, DMSO-$d_6$) δ ppm 9.55 (1H, s), 8.65 (1H, s), 8.46 (1H, s), 8.14 (1H, s), 8.09 (2H, d, J=7.28 Hz), 7.50-7.56 (2H, m), 7.40-7.46 (1H, m), 2.88 (3H, s), 2.78 (3H, s). Mass found 366 [M+H]+.

EXAMPLE 13

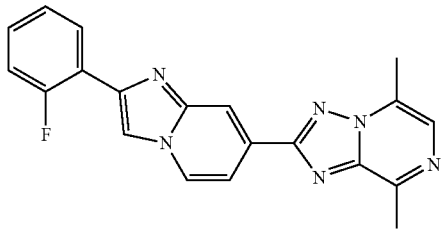 [SMILES: Cc1ncc(C)n2nc(-c3ccn4cc(-c5ccccc5F)nc4c3)nc12]

2-(2-(2-fluorophenyl)imidazo[1,2-a]pyridin-7-yl)-5,8-dimethyl-[1,2,4]-triazolo[1,5-a]pyrazine Example 13 was prepared from 2-bromo-1-(2-fluorophenyl)ethanone following the experimental conditions described in the synthesis of Example 1. The crude solids were collected by filtration and washed with ethanol to give the desired product in 77% yield. $^1$H NMR (400 MHz, DMSO-$d_6$) δ 8.80 (dd, J=7.0, 1.0 Hz, 1H), 8.52 (d, J=4.0 Hz, 1H), 8.41 (s, 1H), 8.37-8.31 (m, 1H), 8.08 (d, J=1.0 Hz, 1H), 7.76 (dd, J=7.2, 1.6 Hz, 1H), 7.49-7.33 (m, 3H), 2.87 (s, 3H), 2.78 (s, 3H). Mass found 358 [M+H]+.

EXAMPLE 14

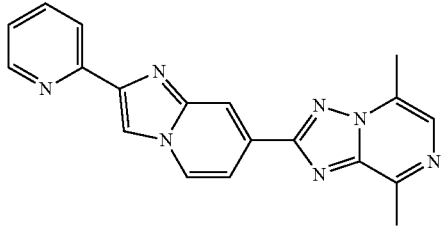 [SMILES: Cc1ncc(C)n2nc(-c3ccn4cc(-c5ccccn5)nc4c3)nc12]

5,8-dimethyl-2-(2-(pyridin-2-yl)imidazo[1,2-a]pyridin-7-yl)-[1,2,4]triazolo[1,5-a]pyrazine Example 14 was prepared from 2-bromo-1-(pyridin-2-yl)ethanone following the experimental conditions described in the synthesis of Example 1. The crude material was purified by HPLC method 12. $^1$H NMR (400 MHz, DMSO-$d_6$) δ 8.80-8.74 (m, 1H), 8.65 (s, 1H), 8.64 (d, J=4.8 Hz, 1H), 8.40 (s, 1H), 8.17 (d, J=7.8 Hz, 1H), 8.07 (d, J=1.0 Hz, 1H), 7.92 (td, J=7.7, 1.8 Hz, 1H), 7.76 (dd, J=7.0, 1.5 Hz, 1H), 7.40-7.33 (m, 1H), 2.86 (s, 3H), 2.77 (s, 3H). Mass found 342 [M+H]+.

EXAMPLE 15

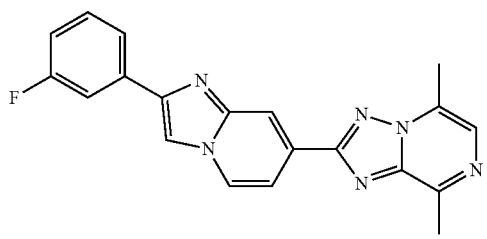 [SMILES: Cc1ncc(C)n2nc(-c3ccn4cc(-c5cccc(F)c5)nc4c3)nc12]

2-(2-(3-fluorophenyl)imidazo[1,2-a]pyridin-7-yl)-5,8-dimethyl-[1,2,4]triazolo[1,5-a]pyrazine Example 15 was prepared from 2-bromo-1-(3-fluorophenyl)ethanone following the experimental conditions described in the synthesis of Example 1. The crude material was purified by HPLC method 12. $^1$H NMR (400 MHz, DMSO-$d_6$) δ 8.70 (d, J=7.0 Hz, 1H), 8.63 (s, 1H), 8.36 (s, 1H), 8.06 (d, J=1.0 Hz, 1H), 7.86 (d, J=7.8 Hz, 1H), 7.80 (d, J=9.3 Hz, 1H), 7.73 (dd, J=7.0, 1.5 Hz, 1H), 7.56-7.48 (m, 1H), 7.22-7.15 (m, 1H), 2.85 (s, 3H), 2.76 (s, 3H). Mass found 359 [M+H]+.

EXAMPLE 16

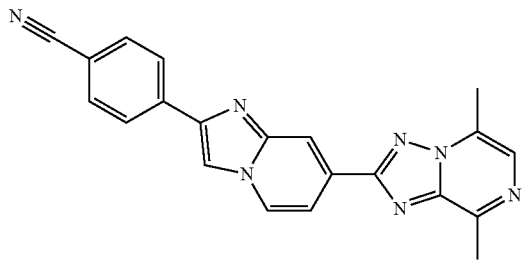 [SMILES: Cc1ncc(C)n2nc(-c3ccn4cc(-c5ccc(C#N)cc5)nc4c3)nc12]

4-(7-(5,8-dimethyl-[1,2,4]triazolo[1,5-a]pyrazin-2-yl)-imidazo[1,2-a]pyridin-2-yl)benzonitrile Example 16 was prepared from 4-(2-bromoacetyl)benzonitrile following the experimental conditions described in the synthesis of Example 1. The crude material was purified by HPLC method 12. $^1$H NMR (400 MHz, DMSO-$d_6$) δ 8.98-8.87 (m, 2H), 8.50 (s, 1H), 8.25 (d, J=8.0 Hz, 2H), 8.11 (s, 1H), 8.03 (d, J=8.3 Hz, 2H), 2.87 (s, 3H), 2.78 (s, 3H). Mass found 366 [M+H]+.

EXAMPLE 17

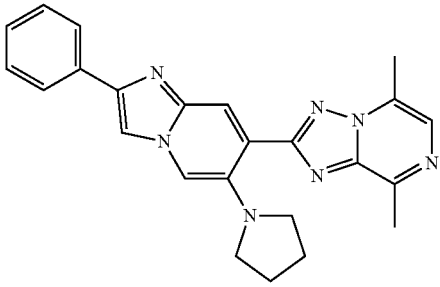 [SMILES: Cc1ncc(C)n2nc(-c3cc4nc(-c5ccccc5)cn4cc3N3CCCC3)nc12]

5,8-dimethyl-2-(2-phenyl-6-(pyrrolidin-1-yl)imidazo
[1,2-a]pyridin-7-yl)-[1,2,4]triazolo[1,5-a]pyrazine A 2.0-5.0 mL microwave vial was charged with 2-(6-bromo-2-phenylimidazo[1,2-a]pyridin-7-yl)-5,8-dimethyl-[1,2,4]triazolo[1,5-a]pyrazine (45 mg, 0.107 mmol) and dissolved in toluene (1073 μL). To that stirring solution was added sodium tert-butoxide (36.1 mg, 0.376 mmol), BINAP (6.68 mg, 10.73 μmol), pyrrolidine (22.90 mg, 0.322 mmol), and palladium(II) acetate (2.410 mg, 10.73 μmol). The vial was sealed and degassed using ultra pure argon under sonication for 1 minute. Once purged, the vial was placed in a reaction block preheated to 110° C. The reaction was let stir overnight. After 19 hours at 110° C. the reaction mixture was cooled to room temperature and diluted with ethyl acetate and water. The contents of the vial were filtered through a pad of diatomaceous earth (Celite®) and the layers were separated. The organic layer was concentrated under reduced pressure to remove excess pyrrolidine and then rediluted with ethyl acetate and transferred into a separatory funnel. The organic was washed with brine (×2), dried with magnesium sulfate, concentrated under reduced pressure, and purified by prepHPLC: Column: Waters XBridge C18 100×30 mm 5 μm, Solvents: water/acetonitrile/TFA, % B gradient (time): 0% (2 min), 0-100% (12 min), 100% (1 min), Flow Rate: 42 mL/min, 3 injections (1 mL DMSO). The desired fractions were collected and neutralized using a saturated solution of sodium bicarbonate and then diluted with ethyl acetate. The layers were separated and the organic was concentrated under reduced pressure and then diluted with methanol and passed through a Phenomenex STRATA-XC 1 g cartridge and was with several volumes of methanol. The product was eluted with 25 mL of 2.0M ammonia in methanol to give 5,8-dimethyl-2-(2-phenyl-6-(pyrrolidin-1-yl)imidazo[1,2-a]pyridin-7-yl)-[1,2,4]triazolo[1,5-a]pyrazine (4.7 mg, 0.01079 mmol, 10% yield) as a yellow solid. $^1$H NMR (400 MHz, DMSO-$d_6$) δ 8.40 (s, 1H), 8.13 (s, 1H), 8.09 (s, 1H), 7.97 (d, J=7.0 Hz, 2H), 7.87 (s, 1H), 7.46 (t, J=7.5 Hz, 2H), 7.38-7.30 (m, 1H), 2.98-2.87 (m, 4H), 2.85 (s, 3H), 2.74 (s, 3H), 1.84-1.78 (m, 4H). Mass found 410 [M+H]+.

INTERMEDIATE 6

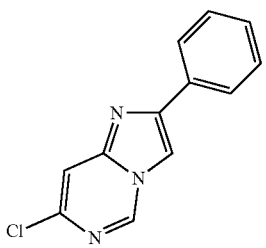 [SMILES: Clc1cc2nc(-c3ccccc3)cn2cn1]

7-chloro-2-phenylimidazo[1,2-c]pyrimidine

A 100 mL round bottom flask was charged with commerically available 6-chloropyrimidin-4-amine (300 mg, 2.316 mmol) and 2-bromo-1-phenylethanone (922 mg, 4.63 mmol). The mixture was suspended in acetonitrile (23.2 mL) and the flask was fitted with a reflux condenser and heated to reflux via heating mantle. The reaction mixture was let stir overnight. After 17 hours, LCMS showed a major peak consistent with desired by mass (m/z=230 [M+H]+); (Methanol/Water/Ammonium Acetate/Phenomenex Luna C18, 30×2 mm, 3μ ES+/−). The reaction mixture was cooled to room temperature and concentrated under reduced pressure. The crude solid was diluted with ethyl acetate and a saturated solution of sodium bicarbonate. The contents of the flask were transferred into a separatory funnel where the aqueous was extracted with ethyl acetate (×3), analyzed for product, and subsequently discarded. The combined organics were transferred into a 125 mL Erlenemyer flask and heated using a heat gun to dissolve the remaining crude. The solution was transferred back into a separatory funnel and the organic was washed with brine (×2), dried with magnesium sulfate, concentrated under reduced pressure and purified by flash chromatography: (40 g SiO$_2$, equilibrated with hexanes, loaded with dichloromethane, initial waste: 125 mL, fraction size: 12 mL 16×100 mm, and eluted with ethyl acetate in hexanes 0% [100 mL], 10% [250 mL], 20% [1000 mL]). Collected product containing fractions to give 7-chloro-2-phenylimidazo[1,2-c]pyrimidine (206 mg, 0.897 mmol, 38.7% yield) as a white solid. $^1$H NMR (400 MHz, DMSO-$d_6$) δ 9.38 (d, J=1.3 Hz, 1H), 8.54 (d, J=0.8 Hz, 1H), 8.06-7.99 (m, 2H), 7.86 (d, J=0.8 Hz, 1H), 7.54-7.45 (m, 2H), 7.44-7.37 (m, 1H). Mass found 230 [M+H]+.

INTERMEDIATE 7

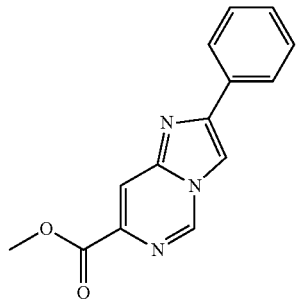 [SMILES: COC(=O)c1cc2nc(-c3ccccc3)cn2cn1]

methyl 2-phenylimidazo[1,2-c]pyrimidine-7-carboxylate

A pressure bomb was charged with 7-chloro-2-phenylimidazo[1,2-c]pyrimidine (835 mg, 3.64 mmol) and dissolved in MeOH (72.70 mL). To that stirring solution was added Hunig's Base (1.00 mL, 5.73 mmol) followed by BINAP (453 mg, 0.727 mmol) and dichlorobis(acetonitrile)palladium(II) (189 mg, 0.727 mmol). The pressure bomb was sealed and the chamber was pressurized to 100 psi using a lecture bottle of carbon monoxide. The reaction chamber was then placed into an oil bath preheated to 60° C. The reaction mixture was let stir overnight. After 19.5 hours, LCMS showed no progress. The reaction vessel was cooled to room temperature and vented. An additional 500 mg of BINAP and 500 mg of the Pd source. The temperature of the oil bath was also raised from 60° C. to 100° C. The pressure bomb was sealed and pressurized to 100 psi using a lecture bottle of carbon monoxide. The reaction container was placed back into the oil bath. After 5.5 hours, LCMS showed significant reaction progress with conversion of starting material to a closely eluting peak consistent with desired product by mass (m/z=254 [M+H]+/Methanol/Water/Ammonium Acetate Phenomenex Luna C18, 30×2 mm, 3µ ES+/−). The product to starting material ratio was approximately 2:1. The reaction was recharged with CO and let stir over the weekend.

After stirring for 70.5 hours, LCMS showed complete consumption of the starting material. Ther reaction mixture was cooled to room temperature and then filtered through a pad of diatomaceous earth (Celite®). The resulting solution was concentrated under reduced pressure and purified by flash chromatography: (40 g SiO$_2$, equilibrated with hexanes, loaded with DCM, fraction size: 12 mL 16×100 mm, and eluted with ethyl acetate in hexanes 0% [250 mL], 40% [250 mL], 60% [1000 mL], 70% [500 mL]). The product containing fractions were collected to give methyl 2-phenylimidazo[1,2-c]pyrimidine-7-carboxylate (500 mg, 1.97 mmol, 54.3% yield) as a brown solid. $^1$H NMR (400 MHz, CHLOROFORM-d) δ 9.13 (d, J=1.3 Hz, 1H), 8.47 (s, 1H), 8.07 (s, 1H), 8.04-7.99 (m, 2H), 7.59-7.40 (m, 4H), 4.07-4.04 (m, 3H). Mass found 254 [M+H]+.

INTERMEDIATE 8

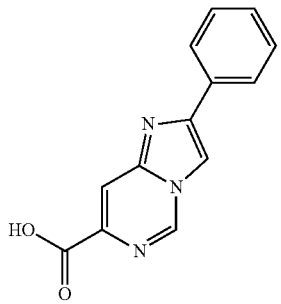 [SMILES: O=C(O)c1cc2nc(-c3ccccc3)cn2cn1]

2-phenylimidazo[1,2-c]pyrimidine-7-carboxylic acid

A 100 mL round bottom flask was charged with methyl 2-phenylimidazo[1,2-c]pyrimidine-7-carboxylate (500 mg, 1.97 mmol) and dissolved in THF (19.70 mL) using sonication. To that stirring solution was added potassium trimethylsilanolate (760 mg, 5.92 mmol). After 30 minutes, TLC showed complete consumption of the starting material. LCMS showed complete consumption of starting material and the formation of a large, more polar peak consistent with the desired product by mass (m/z=240 [M+H]+/Methanol/Water/Ammonium Acetate Phenomenex Luna C18, 30×2 mm, 3µ ES+/−). The mixture was quenched using 10 mL of 4.0M HCl in dioxane. The now yellow slurry was concentrated under reduced pressure. To remove any residual water, 50 mL of acetonitrile was added and the solution was concentrated under reduced pressure. The resulting yellow solid was taken on without any further characterization or purification. Mass found 240 [M+H]+.

EXAMPLE 18

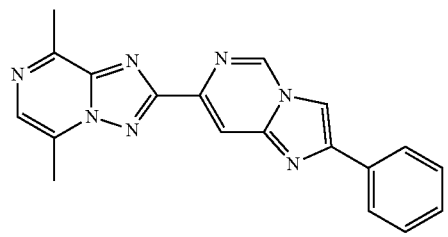

5,8-dimethyl-2-(2-phenylimidazo[1,2-c]pyrimidin-7-yl)-[1,2,4]-triazolo[1,5-a]pyrazine A 75 mL pressure flask was charged with 2-phenylimidazo[1,2-c]pyrimidine-7-carboxylic acid, HCl (544 mg, 1.97 mmol) and suspended in ethyl acetate (9866 µL). To that suspension was added Hunig's Base (2068 µL, 11.84 mmol), 1-amino-3,6-dimethylpyrazin-2(1H)-iminium 2,4,6-trimethylbenzenesulfonate (801 mg, 2.368 mmol), and 1-Propanephosphonic acid cyclic anhydride (5873 µl, 9.87 mmol). The pressure flask was sealed and placed into an oil bath preheated to 80° C. After 30 minutes, LCMS showed a small peak consistent with desired product by mass (m/z=342 [M+H]+/Methanol/Water/Ammonium Acetate Phenomenex Luna C18, 30×2 mm, 3µ ES+/−). The reaction mixture was let stir overnight. After 18 hours at 80° C., LCMS showed only a marginal difference from the 30 minute time point. The mixture was cooled to room temperature and diluted with ethyl acetate and brine. The contents of the flask were transferred into a separatory funnel where the aqueous was extracted with ethyl acetate. Upon extraction a large amount of insoluble material was filtered and the solids were analyzed by LCMS and found to be desired product plus minor impurities. The remaining aqueous was extracted with ethyl acetate and combined with the recovered solids and concentrated under reduced pressure. The crude material was diluted with acetonitrile and reconcentrated. The crude material was dissolved using acetone and dichloromethane and 8 g of silica gel was added and the mixture was concentrated under reduced pressure then purified by flash chromatography: (12 g SiO$_2$, equilibrated with dichloromethane andeluted with methanol in dichloromethane 1% [500 mL], 2% [500 mL], 3% [500 mL]). HPLC analysis showed there still to be a large impurity. The yellow solid was diluted with 12 mL of N,N-dimethylformamide and heated to solubilize then purified by prepHPLC: Column: Waters XBridge C18 100×30 mm 5µ, Solvents: water/acetonitrile/TFA, % B gradient (time): 0% (1 min), 0-100% (15 min), 100% (2 min), Flow Rate: 42 mL/min; 12 runs. The fractions were concentrated and diluted with methanol/DMSO and heated and filtered through a 1 g STRATA-XC cartridge and flushed with several column volumes of methanol. The product was eluted with 25 mL of 2.0M ammonia in methanol. 5,8-dimethyl-2-(2-phenylimidazo[1,2-c]pyrimidin-7-yl)-[1,2,4]triazolo[1,5-a]pyrazine (15 mg, 0.0402 mmol, 2.1% yield). $^1$H NMR (400 MHz, DMSO-d$_6$) δ 9.59 (s, 1H), 8.68 (s, 1H), 8.41 (s, 1H), 8.17-7.98

EXAMPLE 19

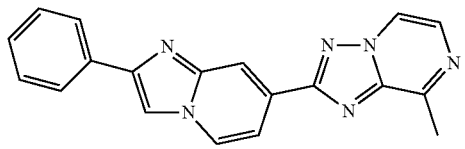 [SMILES: Cc1nccn2nc(-c3ccn4cc(-c5ccccc5)nc4c3)nc12]

8-methyl-2-(2-phenylimidazo[1,2-a]pyridin-7-yl)-1,2,41-triazolo[1,5-a]pyrazine, 2 HCl To a 1 dram vial was added 4-(8-methyl-[1,2,4]triazolo[1,5-a]pyrazin-2-yl)pyridin-2-amine, 2 HCl (100 mg, 0.334 mmol), 2-bromo-1-phenylethanone (100 mg, 0.501 mmol) and Hunig's Base (0.175 mL, 1.003 mmol) in EtOH (2 mL). The vial was sealed and heated to 80° C. overnight. The next day the reaction was checked by LC/MS and was complete. The reaction was acidified with HCl gas and the crude solid was filtered off and washed with cold methanol. The solid was dried in vacuo affording 8-methyl-2-(2-phenylimidazo[1,2-a]pyridin-7-yl)-[1,2,4]triazolo[1,5-a]pyrazine, 2 HCl (51 mg, 0.126 mmol, 37.8% yield) as a tan solid. $^1$H NMR (400 MHz, METHANOL-$d_4$) δ 8.99 (dd, J=7.0, 1.0 Hz, 1H), 8.87 (d, J=4.5 Hz, 1H), 8.81-8.67 (m, 2H), 8.38 (dd, J=7.0, 1.5 Hz, 1H), 8.19 (d, J=4.5 Hz, 1H), 7.97 (dd, J=7.9, 1.4 Hz, 2H), 7.75-7.54 (m, 3H), 3.01 (s, 3H), LC/Mass spec. (Method 1) RT=1.98 min. Mass=327.2 (MH)$^+$.

EXAMPLE 20

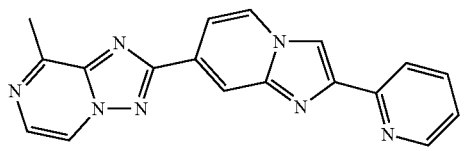 [SMILES: Cc1nccn2nc(-c3ccn4cc(-c5ccccn5)nc4c3)nc12]

8-methyl-2-(2-(pyridin-2-yl)imidazo[1,2-a]pyridin-7-yl)-[1,2,4]triazolo[1,5-a]pyrazine, 2 HCl To a 1 dram vial was added 4-(8-methyl-[1,2,4]triazolo[1,5-a]pyrazin-2-yl)pyridin-2-amine (22 mg, 0.097 mmol), 2-bromo-1-(pyridin-2-yl)ethanone, hydrobromide (43.7 mg, 0.156 mmol) and Hunig's Base (0.051 mL, 0.292 mmol) in EtOH (1 mL). The vial was sealed and heated to 80° C. overnight. The next day the reaction was checked by LC/MS and was complete. The crude solid was filtered off and washed with cold ethanol. The solid was dried in vacuo. The crude solid was then dissolved in hot methanol and then HCl gas was bubbled in to convert it to the HCl salt. The solvent was then evaporated in vacuo affording 8-methyl-2-(2-(pyridin-2-yl)imidazo[1,2-a]pyridin-7-yl)-[1,2,4]triazolo[1,5-a]pyrazine, 2 HCl (15 mg, 0.037 mmol, 37.8% yield) as a tan solid. $^1$H NMR (400 MHz, METHANOL-$d_4$) δ 9.52 (d, J=5.3 Hz, 1H), 9.18 (s, 1H), 9.14 (d, J=6.5 Hz, 1H), 8.97 (d, J=5.0 Hz, 1H), 8.92 (s, 1H), 8.59-8.51 (m, 2H), 8.47 (d, J=5.3 Hz, 1H), 8.40 (d, J=7.3 Hz, 1H), 7.97 (br. s., 1H), 3.31 (br. s., 3H), LC/Mass spec. (Method 1) RT=1.81 min. Mass=328.3 (MH)$^+$.

EXAMPLE 21

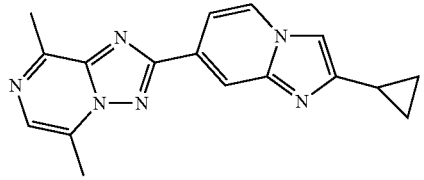 [SMILES: Cc1ncc(C)n2nc(-c3ccn4cc(C5CC5)nc4c3)nc12]

2-(2-cyclopropylimidazo[1,2-a]pyridin-7-yl)-5,8-dimethyl-[1,2,4]triazolo[1,5-a]pyrazine To a 1 dram vial was added 4-(5,8-dimethyl-[1,2,4]triazolo[1,5-a]pyrazin-2-yl)pyridin-2-amine, 2 HCl (60 mg, 0.192 mmol), 2-bromo-1-cyclopropylethanone (43.7 mg, 0.268 mmol) and Hunig's Base (0.134 mL, 0.766 mmol) in EtOH (1 mL). The vial was sealed and heated to 90° C. overnight. The next day the reaction was checked by LC/MS and was complete. The reaction was cooled to rt and the solvent was evaporated in vacuo. The crude oil was loaded onto a silica gel column and eluted with 1% methanol/99% CH2Cl2. The pure fractions were combined and evaporated in vacuo affording 2-(2-cyclopropylimidazo[1,2-a]pyridin-7-yl)-5,8-dimethyl-[1,2,4]triazolo[1,5-a]pyrazine (37 mg, 0.119 mmol, 61.9% yield). $^1$H NMR (400 MHz, METHANOL-$d_4$) δ 8.37 (dd, J=7.0, 1.0 Hz, 1H), 8.29-8.22 (m, 1H), 7.88 (d, J=1.0 Hz, 1H), 7.67 (dd, J=7.0, 1.5 Hz, 1H), 7.65 (s, 1H), 2.91-2.83 (m, 3H), 2.78 (s, 3H), 2.16-1.95 (m, 1H), 1.04 (d, J=8.5 Hz, 2H), 0.93 (dd, J=4.8, 2.3 Hz, 2H), LC/Mass spec. (Method 1) RT=1.97 min. Mass=305.2 (MH)$^+$.

EXAMPLE 22

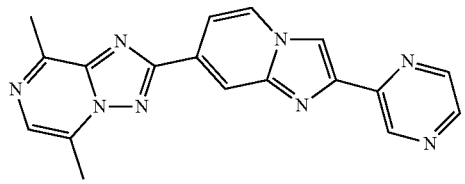 [SMILES: Cc1ncc(C)n2nc(-c3ccn4cc(-c5cnccn5)nc4c3)nc12]

5,8-dimethyl-2-(2-(pyrazin-2-yl)imidazo[1,2-a]pyridin-7-yl)-[1,2,4]triazolo[1,5-a]pyrazine To a 1 dram vial was added 4-(5,8-dimethyl-[1,2,4]triazolo[1,5-a]pyrazin-2-yl)pyridin-2-amine, 2 HCl (50 mg, 0.160 mmol), 2-bromo-1-(pyrazin-2-yl)ethanone (48.1 mg, 0.239 mmol) and Hunig's Base (0.112 mL, 0.639 mmol) in EtOH (1 mL). The vial was sealed and heated to 90° C. overnight. The next day the reaction was cooled to rt and analyzed by LC/MS. The reaction was complete and the solution was cooled to rt and the crude solid was filtered off and washed with cold Ethanol. The resulting solid was pure by LC/MS. The solid was then dissolved in hot methanol containing TFA. The solvent was then evaporated in vacuo affording 5,8-dimethyl-2-(2-(pyrazin-2-yl)imidazo[1,2-a]pyridin-7-yl)-[1, 2,4]triazolo[1,5-a]pyrazine, 2 TFA (48 mg, 0.077 mmol, 48.5% yield). $^1$H NMR (400 MHz, DMSO-$d_6$) δ 9.35 (s, 1H), 8.80 (d, J=7.3 Hz, 1H), 8.75 (s, 1H), 8.72 (s, 1H), 8.64 (d, J=2.5 Hz, 1H), 8.43 (s, 1H), 8.08 (s, 1H), 7.79 (d, J=6.8 Hz, 1H), 2.87 (s, 3H), 2.78 (s, 3H), LC/Mass spec. (Method 1) RT=1.87 min. Mass=343.3 (MH)$^+$.

EXAMPLE 23

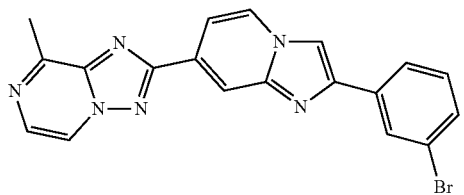 [SMILES: Cc1nccn2nc(-c3ccn4cc(-c5cccc(Br)c5)nc4c3)nc12]

2-(2-(3-bromophenyl)imidazo[1,2-a]pyridin-7-yl)-8-methyl-[1,2,4]triazolo[1,5-a]pyrazine To a 1 dram vial was added 4-(8-methyl-[1,2,4]triazolo[1,5-a]pyrazin-2-yl)pyridin-2-amine, 2 HCl (150 mg, 0.501 mmol), 2-bromo-1-(3-bromophenyl)ethanone (167 mg, 0.602 mmol), and Hunig's Base (0.350 mL, 2.006 mmol) in EtOH (2 mL). The vial was sealed and heated to 90° C. and allowed to stir overnight. The next day the reaction was analyzed by LC/MS and was complete. The reaction solvent was evaporated in vacuo and the crude solid was loaded onto a silica gel column and eluted with 2% MeOH/98% $CH_2Cl_2$. The pure fractions were combined and evaporated in vacuo affording 2-(2-(3-bromophenyl)imidazo[1,2-a]pyridin-7-yl)-8-methyl-[1,2,4]triazolo[1,5-a]pyrazine (190 mg, 0.445 mmol, 89% yield) as a brown solid. $^1$H NMR (400 MHz, CHLOROFORM-d) δ 8.68 (s, 1H), 8.44 (dd, J=4.5, 0.5 Hz, 1H), 8.28 (d, J=7.0 Hz, 1H), 8.17 (t, J=1.8 Hz, 1H), 8.08 (d, J=4.5 Hz, 1H), 8.01-7.94 (m, 2H), 7.81 (d, J=7.0 Hz, 1H), 7.50 (ddd, J=7.9, 1.9, 1.0 Hz, 1H), 7.35 (t, J=7.9 Hz, 1H), 3.07-2.96 (m, 3H), LC/Mass spec. (Method 1) RT=2.62 min. Mass=405.1 (MH)$^+$.

EXAMPLE 24

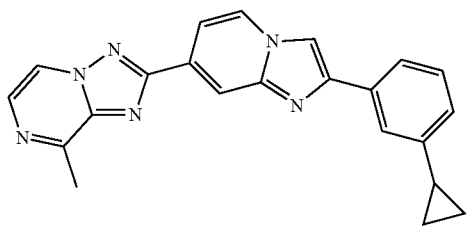 [SMILES: Cc1nccn2nc(-c3ccn4cc(-c5cccc(C6CC6)c5)nc4c3)nc12]

2-(2-(3-cyclopropylphenyl)imidazo[1,2-a]pyridin-7-yl)-8-methyl-[1,2,4]triazolo[1,5-a]pyrazine To a microwave vial was added 2-(2-(3-bromophenyl)imidazo[1,2-a]pyridin-7-yl)-8-methyl-[1,2,4]triazolo[1,5-a]pyrazine (35 mg, 0.086 mmol), cyclopropylboronic acid (22.26 mg, 0.259 mmol), TRICYCLOHEXYLPHOSPHINE (12.11 mg, 0.043 mmol), Toluene (1 mL), Water (0.3 mL) and Potassium phosphate tribasic (73.3 mg, 0.345 mmol). The solution was purged with nitrogen for 5 min and then PALLADIUM(II) ACETATE (1.939 mg, 8.64 µmol) was added. The reaction vial was sealed and heated to 110° C. for 2 hours. The reaction turned black and was then checked by LC/MS. The reaction was complete as indicated by no starting bromide being present. The reaction was cooled to rt and extracted with EtOAc 4×. The organic fractions were combined, dried over $Na_2SO_4$ and evaporated in vacuo. The crude oil was purified by silica gel chromatography eluting with 1% MeOH/99% $CH_2Cl_2$. The pure fractions were combined and evaporated in vacuo affording 2-(2-(3-cyclopropylphenyl)imidazo[1,2-a]pyridin-7-yl)-8-methyl-[1,2,4]triazolo[1,5-a]pyrazine (24 mg, 0.065 mmol, 75% yield) as an off white solid. $^1$H NMR (400 MHz, CHLOROFORM-d) δ 8.67 (br. s., 1H), 8.43 (d, J=4.5 Hz, 1H), 8.25 (d, J=5.3 Hz, 1H), 8.06 (d, J=4.5 Hz, 1H), 7.95 (s, 1H), 7.82-7.68 (m, 3H), 7.35 (t, J=7.7 Hz, 1H), 7.08 (d, J=7.5 Hz, 1H), 3.01 (s, 3H), 2.08-1.97 (m, 1H), 1.09-0.96 (m, 2H), 0.90-0.75 (m, 2H), LC/Mass spec. (Method 1) RT=2.20 min. Mass=367.2 (MH)$^+$.

EXAMPLE 25

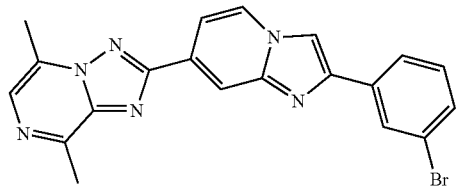 [SMILES: Cc1ncc(C)n2nc(-c3ccn4cc(-c5cccc(Br)c5)nc4c3)nc12]

2-(2-(3-bromophenyl)imidazo[1,2-a]pyridin-7-yl)-5,8-dimethyl-[1,2,4]triazolo[1,5-a]pyrazine To a 1 dram vial was added 4-(5,8-dimethyl-[1,2,4]triazolo[1,5-a]pyrazin-2-yl)pyridin-2-amine, 2 HCl (170 mg, 0.543 mmol), 2-bromo-1-(3-bromophenyl)ethanone (196 mg, 0.706 mmol), and Hunig's Base (0.379 mL, 2.171 mmol) in EtOH (2 mL). The vial was sealed and heated to 90° C. and allowed to stir overnight. The next day the reaction was analyzed by LC/MS and was complete. The reaction solvent was evaporated in vacuo and the crude solid was loaded onto a silica gel column and eluted with 2% MeOH/98% $CH_2Cl_2$. The pure fractions were combined and evaporated in vacuo affording 2-(2-(3-bromophenyl)imidazo[1,2-a]pyridin-7-yl)-5,8-dimethyl-[1,2,4]triazolo[1,5-a]pyrazine (173 mg, 0.408 mmol, 75% yield) as a brown solid. $^1$H NMR (400 MHz, CHLOROFORM-d) δ 9.11 (br. s., 1H), 8.59 (br. s., 1H), 8.16 (s, 1H), 7.26-7.14 (m, 3H), 7.11-7.03 (m, 1H), 2.83 (s, 3H), 2.72 (s, 3H), LC/Mass spec. (Method 1) RT=2.25 min. Mass=419.1 (MH)$^+$.

EXAMPLE 26

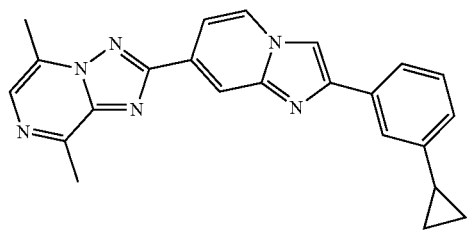 [SMILES: Cc1ncc(C)n2nc(-c3ccn4cc(-c5cccc(C6CC6)c5)nc4c3)nc12]

2-(2-(3-cyclopropylphenyl)imidazo[1,2-a]pyridin-7-yl)-5,8-dimethyl-1,2,41-triazolo[1,5-a]pyrazine To a microwave vial was added 2-(2-(3-bromophenyl)imidazo[1,2-a]pyridin-7-yl)-5,8-dimethyl-[1,2,4]triazolo[1,5-a]pyrazine (37 mg, 0.088 mmol), cyclopropylboronic acid (22.74 mg, 0.265 mmol), TRICYCLOHEXYLPHOSPHINE (12.37 mg, 0.044 mmol), Toluene (1 mL), Water (0.3 mL) and potassium phosphate tribasic (74.9 mg, 0.353 mmol). The solution was purged with nitrogen for 5 min and then PALLADIUM(II) ACETATE (1.981 mg, 8.82 µmol) was added. The reaction vial was sealed and heated to 110° C. for 16 hours. The reaction turned black and was checked by LC/MS. The reaction was complete as indicated by no starting bromide being present. The reaction was cooled to rt and extracted with EtOAc 4×. The organic fractions were combined, dried over Na2SO4 and evaporated in vacuo. The crude oil was purified by silica gel chromatography eluting with 5% Acetone/95% Hexanes to 60% Acetone/40% Hexanes. The pure fractions were combined and evaporated in vacuo affording 2-(2-(3-cyclopropylphenyl)imidazo[1,2-a]pyridin-7-yl)-5,8-dimethyl-[1,2,4]triazolo[1,5-a]pyrazine (24 mg, 0.058 mmol, 66.1% yield) as an off white solid. $^1$H NMR (400 MHz, CHLOROFORM-d) δ 8.79 (br. s., 1H), 8.29 (d, J=4.5 Hz, 1H), 7.97 (s, 1H), 7.92 (s, 1H), 7.81 (s, 1H), 7.78 (d, J=4.5 Hz, 1H), 7.38 (t, J=4.5 Hz, 1H), 7.10 (d, J=4.5 Hz, 1H), 2.98 (s, 3H), 2.82 (s, 3H), 2.01 (m, 1H), 1.02 (m, 2H), 0.86 (m, 2H), LC/Mass spec. (Method 1) RT=1.89 min. Mass=381.2 (MH)$^+$.

EXAMPLE 27

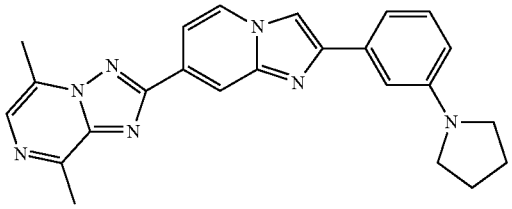 [SMILES: Cc1ncc(C)n2nc(-c3ccn4cc(-c5cccc(N6CCCC6)c5)nc4c3)nc12]

5,8-dimethyl-2-(2-(3-(pyrrolidin-1-yl)phenyl)imidazo[1,2-a]pyridin-7-yl)-[1,2,4]triazolo[1,5-a]pyrazine To a microwave vial was added 2-(2-(3-bromophenyl)imidazo[1,2-a]pyridin-7-yl)-5,8-dimethyl-[1,2,4]triazolo[1,5-a]pyrazine (37 mg, 0.088 mmol), pyrrolidine (18.83 mg, 0.265 mmol), SODIUM TERT-BUTOXIDE (29.7 mg, 0.309 mmol), BINAP (5.49 mg, 8.82 mmol), and Toluene (1 mL). The solution was purged with nitrogen for 5 min and then PALLADIUM(II) ACETATE (0.991 mg, 4.41 mmol) was added. The reaction vial was sealed and heated to 100° C. for 16 hours. The reaction turned black and was then checked by LC/MS. The reaction was complete as indicated by no starting bromide being present. The reaction was cooled to rt diluted with saturated NH4Cl and extracted with EtOAc 4×. The organic fractions were combined, dried over Na2SO4 and evaporated in vacuo. The crude oil was purified by silica gel chromatography eluting with 5% Acetone/95% Hexanes to 60% Acetone/40% Hexanes. The pure fractions were combined and evaporated in vacuo affording 5,8-dimethyl-2-(2-(3-(pyrrolidin-1-yl)phenyl)imidazo[1,2-a]pyridin-7-yl)-[1,2,4]triazolo[1,5-a]pyrazine (21.9 mg, 0.048 mmol, 53.9% yield) as a tan solid. $^1$H NMR (400 MHz, CHLOROFORM-d) δ 8.71 (s, 1H), 8.23 (dd, J=7.0, 1.5 Hz, 1H), 7.96-7.92 (m, 1H), 7.89 (d, J=1.0 Hz, 1H), 7.78 (dd, J=7.0, 1.5 Hz, 1H), 7.35-7.28 (m, 2H), 7.26-7.18 (m, 1H), 6.66-6.54 (m, 1H), 3.48-3.33 (m, 4H), 2.97 (s, 3H), 2.80 (s, 3H), 2.06 (m, 4H), LC/Mass spec. (Method 1) RT=2.32 min. Mass=410.2 (MH)$^+$.

EXAMPLE 28

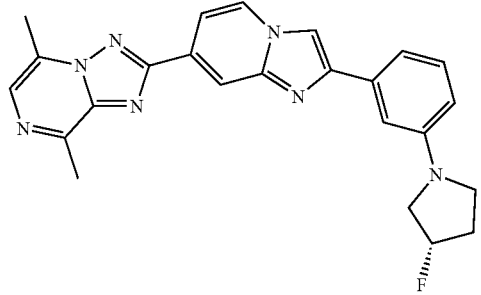 [SMILES: Cc1ncc(C)n2nc(-c3ccn4cc(-c5cccc(N6CC[C@H](F)C6)c5)nc4c3)nc12]

(S)-2-(2-(3-(3-fluoropyrrolidin-1-yl)phenyl)imidazo[1,2-a]pyridin-7-yl)-5,8-dimethyl-[1,2,4]triazolo[1,5-a]pyrazine To a microwave vial was added 2-(2-(3-bromophenyl)imidazo[1,2-a]pyridin-7-yl)-5,8-dimethyl-[1,2,4]triazolo[1,5-a]pyrazine (39 mg, 0.093 mmol), (S)-3-fluoropyrrolidine, HCl (35.0 mg, 0.279 mmol), SODIUM TERT-BUTOXIDE (44.7 mg, 0.465 mmol), BINAP (5.79 mg, 9.30 µmol), and Toluene (1 mL). The solution was purged with nitrogen for 5 min and then PALLADIUM(II) ACETATE (1.044 mg, 4.65 µmol) was added. The reaction vial was sealed and heated to 100° C. for 16 hours. The reaction turned black and was then checked by LC/MS. The reaction was complete as indicated by no starting bromide being present. The reaction was cooled to rt, diluted with saturated NH4Cl and extracted with EtOAc 4×. The organic fractions were combined, dried over Na2SO4 and evaporated in vacuo. The crude oil was purified by silica gel chromatography eluting with 1% MeOH/99% CH$_2$Cl$_2$. The pure fractions were combined and evaporated in vacuo affording (S)-2-(2-(3-(3-fluoropyrrolidin-1-yl)phenyl)imidazo[1,2-a]pyridin-7-yl)-5,8-dimethyl-[1,2,4]triazolo[1,5-a]pyrazine (24 mg, 0.055 mmol, 59.2% yield) as a yellow solid. $^1$H NMR (400 MHz, CHLOROFORM-d) δ 8.71 (s, 1H), 8.23 (d, J=7.0 Hz, 1H), 7.93 (s, 1H), 7.89 (s, 1H), 7.79 (d, J=7.0 Hz, 1H), 7.32 (t, J=7.8 Hz, 2H), 7.26 (d, J=7.8 Hz, 1H), 6.60 (dd, J=7.9, 1.6 Hz, 1H), 5.50-5.36 (m, 1H), 3.80-3.71 (m, 1H), 3.66 (s, 1H), 3.60 (dd, J=9.5, 4.3 Hz, 2H), 2.97 (s, 3H), 2.80 (s, 3H), 2.51-2.33 (m, 1H), 2.33-2.08 (m, 1H), LC/Mass spec. (Method 1) RT=2.39 min. Mass=428.3 (MH)$^+$.

EXAMPLE 29

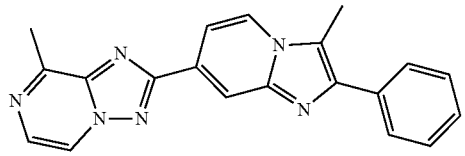 [SMILES: Cc1nccn2nc(-c3ccn4c(C)c(-c5ccccc5)nc4c3)nc12]

8-methyl-2-(3-methyl-2-phenylimidazo[1,2-a]pyridin-7-yl)-[1,2,4]triazolo[1,5-a]pyrazine 2-Bromopropiophenone (0.034 ml, 0.221 mmol) was added to a solution of 4-(8-methyl-[1,2,4]triazolo[1,5-a]pyrazin-2-yl)pyridin-2-amine (0.025 g, 0.111 mmol) in Ethanol (2.2 ml) and the mixture was heated at 80° C. for 40 hours. LC/MS analysis of the reaction mixture indicates reaction approximately 40% complete. The reaction mixture was transferred to a microwave reaction tube and N,N-diisopropylethylamine (0.059 ml, 0.332 mmol) was added. The reaction mixture was heated at 110° C. under standard microwave conditions for 2 hours. LC/MS analysis indicates reaction completion. The reaction mixture was concentrated in vacuo. The crude product was purified by flash chromatography (silica gel; 30-100% EtOAc/hexanes) to afford a tan solid (0.007 g, 0.020 mmol, 18.05% yield). $^1$H NMR (400 MHz, METHANOL-d$_4$) δ 8.76 (d, J=4.5 Hz, 1H), 8.51 (s, 1H), 8.42 (d, J=6.5 Hz, 1H), 8.08 (d, J=4.5 Hz, 1H), 7.90 (dd, J=7.2, 1.6 Hz, 1H), 7.82-7.75 (m, 2H), 7.52 (t, J=7.5 Hz, 2H), 7.42 (s, 1H), 2.97 (s, 3H), 2.73 (s, 3H), LC/MS: (Method 2) Anal. Calcd. for [M+H]$^+$C$_{20}$H$_{17}$N$_6$: 341.15. Found: 341.07.

EXAMPLE 30

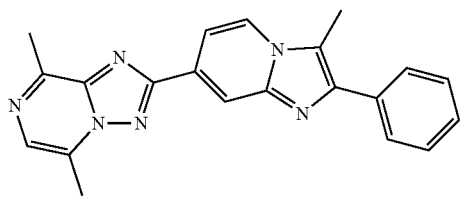 [SMILES: Cc1ncc(C)n2nc(-c3ccn4c(C)c(-c5ccccc5)nc4c3)nc12]

5,8-dimethyl-2-(3-methyl-2-phenylimidazo[1,2-a]pyridin-7-yl)-[1,2,4]triazolo[1,5-a]pyrazine, 2 TFA 2-bromo-1-phenylpropan-1-one (0.032 ml, 0.208 mmol) was added to a solution of 4-(5,8-dimethyl-[1,2,4]triazolo[1,5-a]pyrazin-2-yl)pyridin-2-amine (0.025 mg, 0.104 mmol) and N-ethyl-N-isopropylpropan-2-amine (0.056 ml, 0.312 mmol) in EtOH (2.5 mL) and the mixture was heated under standard microwave conditions at 110° C. for 4 hours. LC/MS analysis of the reaction mixture indicates reaction completion. The reaction mixture was concentrated in vacuo. The crude product was purified by flash chromatography (silica gel; 30-100% EtOAc/hexanes) to afford a yellow solid. The purified product was dissolved in 5 mL of a 1:1 solution of dichloromethane and trifluoroacetic acid. This mixture was allowed to stir overnight at room temperature. The volatiles were removed in vacuo to give 5,8-dimethyl-2-(3-methyl-2-phenylimidazo[1,2-a]pyridin-7-yl)-[1,2,4]triazolo[1,5-a]pyrazine, 2 TFA (0.0112 g, 0.019 mmol, 18.5% yield) as a white solid. $^1$H NMR (400 MHz, DMSO-d$_6$) δ 8.55 (d, J=7.5 Hz, 1H), 8.40 (s, 1H), 8.08 (s, 1H), 7.87 (d, J=7.0 Hz, 2H), 7.78 (dd, J=7.0, 1.8 Hz, 1H), 7.53 (t, J=7.7 Hz, 2H), 7.42 (d, J=7.3 Hz, 1H), 2.87 (s, 3H), 2.78 (s, 3H), 2.74 (s, 3H), LC/MS: (Method 2) Anal. Calcd. for [M+H]$^+$C$_{21}$H$_{19}$N$_6$: 355.16. Found: 355.18.

BIOLOGICAL STUDIES

LE_PDE10A Inhibition Assay:

The PDE10 inhibition assay in 384-well plates was conducted to identify substances for the inhibition of cyclic nucleotide hydrolysis by the PDE10 enzyme. The cyclic nucleotide substrate concentration used was at a K$_m$ concentration (25 nM final). PDE10 activity was measured using Scintillation Proximity Assay (SPA)-based methods. PDE10 catalyses the hydrolysis of the intracellular messenger adenosine 5',8'-cyclic phosphate (cAMP) to the non-cyclic adenosine 5'-monophosphate (AMP). The SPA assay was based upon the selective interaction of the tritiated product with yttrium oxide LEADseeker beads.

The assay was performed in 10 μL samples containing 5 μL of 0.3 ng/mL PDE10 final and 5 μL of 3$^H$-5',8' cAMP (PerkinElmer, NET111540) run at K$_m$ of 25 nM final. The assay buffer contained 25 mM HEPES pH 7.4, 2.5 mM Magnesium Chloride and 0.1% BSA. Compound dose response curves were pre-incubated with 5 L of 2×PDE10 enzyme for 10 minutes prior to adding 5 ul of 2×K$_m$ substrate for 30 minutes. The reaction was terminated by adding 6 μL of 5 mg/mL of yttrium oxide LEADseeker beads. The beads were allowed to settle for 3 hours before plates were read in the LEEDSeaker for 6 minutes. The measured signal could be converted to activity relative to an inhibited control (100%). IC50 values were calculated by using in-house data software and IC50 values were generated by nonlinear regression analysis. (Bristol-Myers Squibb Company, Wallingford, Conn.).

Table 1 shows the IC50 values of the compounds of the present disclosure. Ranges are as follows: A=0.0001-1.0 nM; B=1.0-100 nM; C>100 nM.

TABLE 1

| Example | Structure | PDE10 IC$_{50}$ (Range) | PDE10 IC$_{50}$ (nM) |
|---|---|---|---|
| 1 | 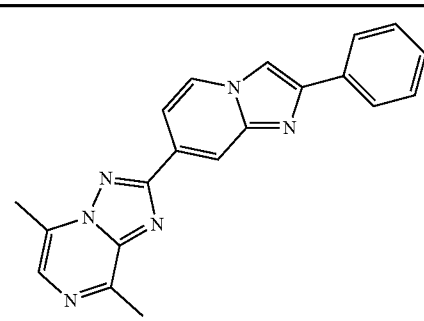 | A | 0.10 |

TABLE 1-continued

| Example | Structure | PDE10 IC$_{50}$ (Range) | PDE10 IC$_{50}$ (nM) |
|---------|-----------|-------------------------|----------------------|
| 2 | 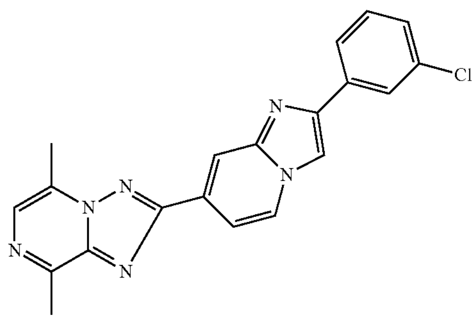 [SMILES: Cc1ncc(C)n2nc(-c3ccn4cc(-c5cccc(Cl)c5)nc4c3)nc12] | A | |
| 4 | 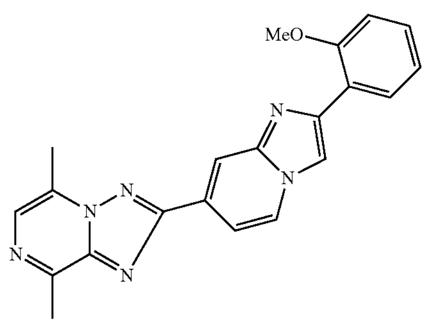 [SMILES: COc1ccccc1-c1cn2ccc(-c3nc4c(C)ncc(C)n4n3)cc2n1] | | |
| 5 | 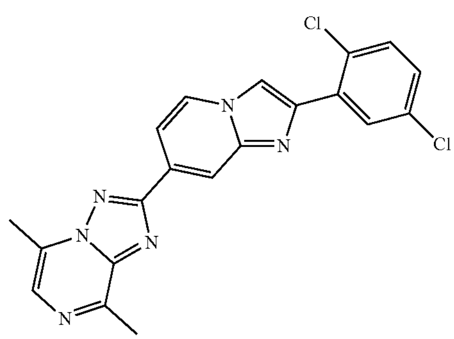 [SMILES: Cc1ncc(C)n2nc(-c3ccn4cc(-c5cc(Cl)ccc5Cl)nc4c3)nc12] | | |
| 6 | 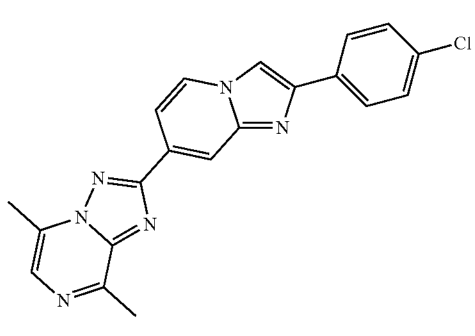 [SMILES: Cc1ncc(C)n2nc(-c3ccn4cc(-c5ccc(Cl)cc5)nc4c3)nc12] | B | |

TABLE 1-continued

| Example | Structure | PDE10 IC$_{50}$ (Range) | PDE10 IC$_{50}$ (nM) |
|---|---|---|---|
| 7 | 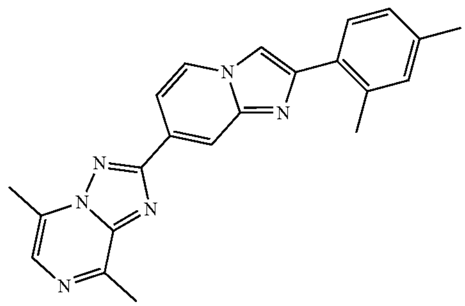 | B | 11 |
| 8 | 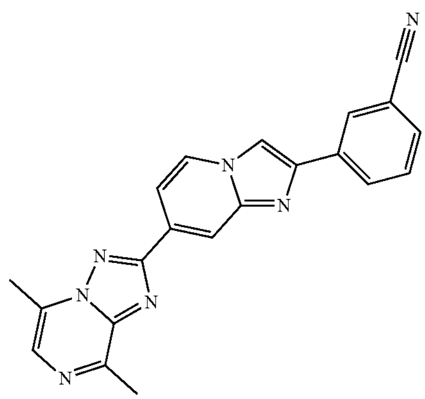 [SMILES: Cc1ncc(C)n2nc(-c3ccn4cc(-c5cccc(C#N)c5)nc4c3)nc12] | | |
| 9 | 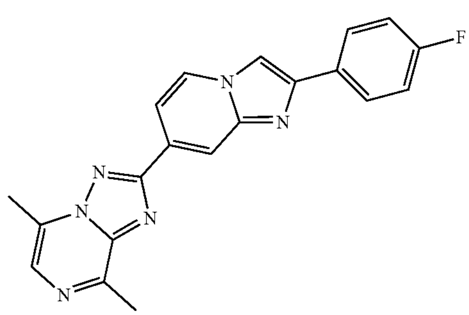 [SMILES: Cc1ncc(C)n2nc(-c3ccn4cc(-c5ccc(F)cc5)nc4c3)nc12] | A | |
| 10 | 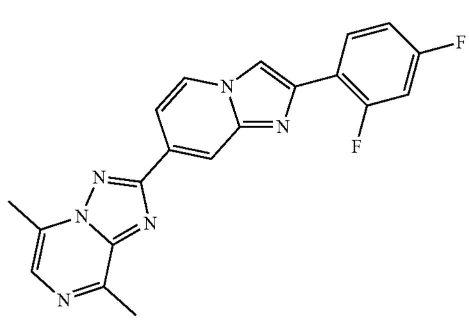 [SMILES: Cc1ncc(C)n2nc(-c3ccn4cc(-c5ccc(F)cc5F)nc4c3)nc12] | | |

TABLE 1-continued

| Example | Structure | PDE10 IC$_{50}$ (Range) | PDE10 IC$_{50}$ (nM) |
|---|---|---|---|
| 11 | 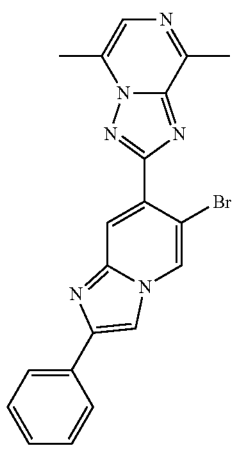 [SMILES: Cc1ncc(C)n2nc(-c3cc4nc(-c5ccccc5)cn4cc3Br)nc12] | A | |
| 12 | 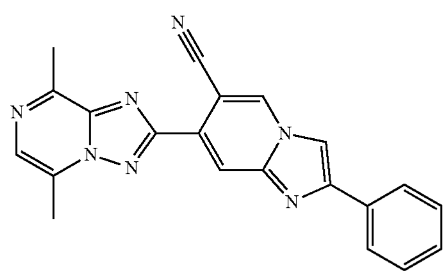 [SMILES: Cc1ncc(C)n2nc(-c3cc4nc(-c5ccccc5)cn4cc3C#N)nc12] | A | |
| 13 | 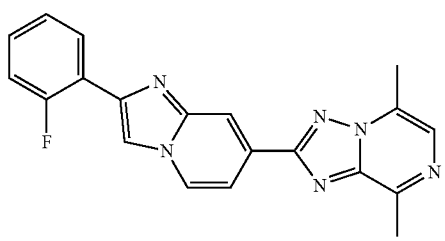 [SMILES: Cc1ncc(C)n2nc(-c3ccn4cc(-c5ccccc5F)nc4c3)nc12] | A | |
| 14 | 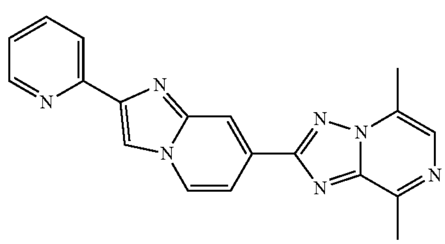 [SMILES: Cc1ncc(C)n2nc(-c3ccn4cc(-c5ccccn5)nc4c3)nc12] | A | 0.16 |
| 15 | 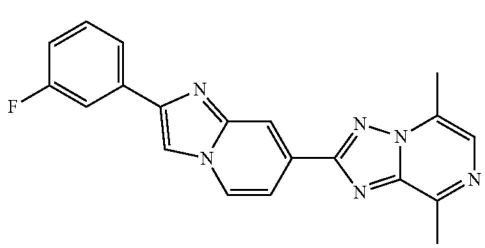 [SMILES: Cc1ncc(C)n2nc(-c3ccn4cc(-c5cccc(F)c5)nc4c3)nc12] | A | |

TABLE 1-continued

| Example | Structure | PDE10 IC$_{50}$ (Range) | PDE10 IC$_{50}$ (nM) |
|---|---|---|---|
| 16 | 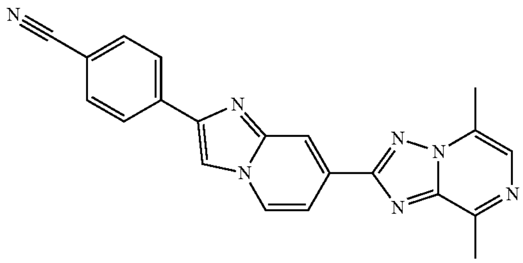 [SMILES: Cc1ncc(C)n2nc(-c3ccn4cc(-c5ccc(C#N)cc5)nc4c3)nc12] | B | |
| 17 | 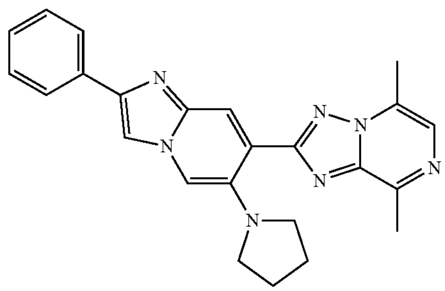 [SMILES: Cc1ncc(C)n2nc(-c3cc4nc(-c5ccccc5)cn4cc3N3CCCC3)nc12] | B | 3.5 |
| 18 | 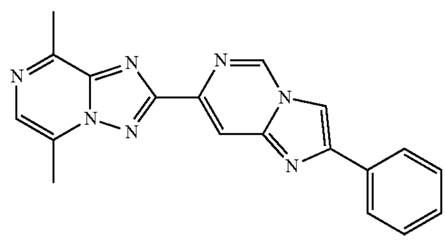 [SMILES: Cc1ncc(C)n2nc(-c3cc4nc(-c5ccccc5)cn4cn3)nc12] | A | |
| 19 | 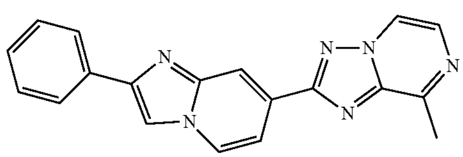 [SMILES: Cc1nccn2nc(-c3ccn4cc(-c5ccccc5)nc4c3)nc12] | B | |
| 20 | 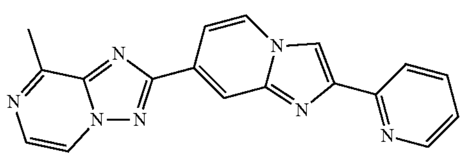 [SMILES: Cc1nccn2nc(-c3ccn4cc(-c5ccccn5)nc4c3)nc12] | B | |
| 21 | 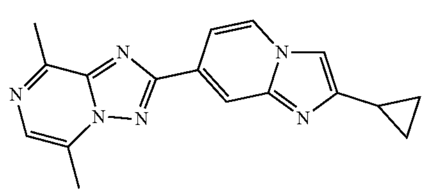 [SMILES: Cc1ncc(C)n2nc(-c3ccn4cc(C5CC5)nc4c3)nc12] | B | 26 |
| 22 | 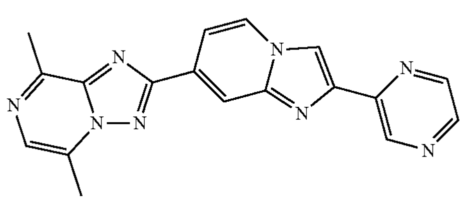 [SMILES: Cc1ncc(C)n2nc(-c3ccn4cc(-c5cnccn5)nc4c3)nc12] | B | |

TABLE 1-continued

| Example | Structure | PDE10 IC$_{50}$ (Range) | PDE10 IC$_{50}$ (nM) |
|---|---|---|---|
| 23 | 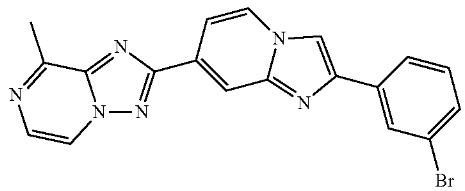 [SMILES: Cc1nccn2nc(-c3ccn4cc(-c5cccc(Br)c5)nc4c3)nc12] | B | |
| 24 | 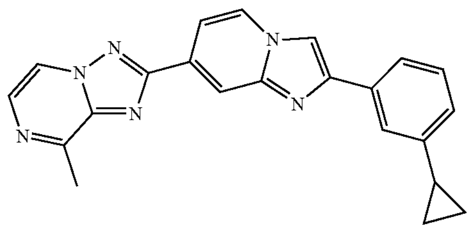 [SMILES: Cc1nccn2nc(-c3ccn4cc(-c5cccc(C6CC6)c5)nc4c3)nc12] | B | |
| 25 | 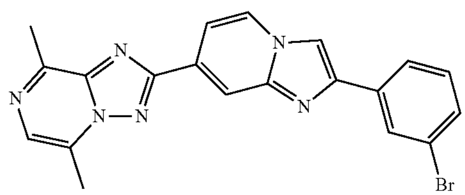 [SMILES: Cc1ncc(C)n2nc(-c3ccn4cc(-c5cccc(Br)c5)nc4c3)nc12] | A | |
| 26 | 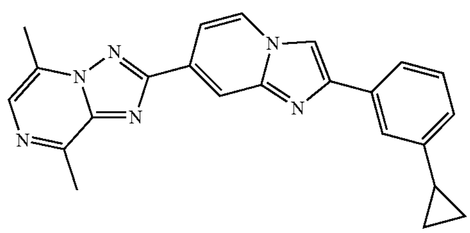 [SMILES: Cc1ncc(C)n2nc(-c3ccn4cc(-c5cccc(C6CC6)c5)nc4c3)nc12] | A | 0.33 |
| 27 | 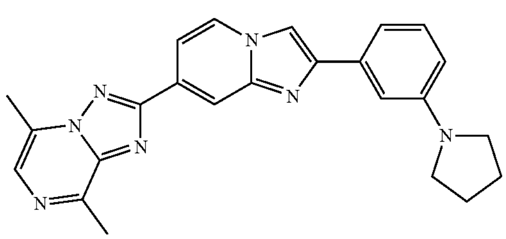 [SMILES: Cc1ncc(C)n2nc(-c3ccn4cc(-c5cccc(N6CCCC6)c5)nc4c3)nc12] | A | |
| 28 | 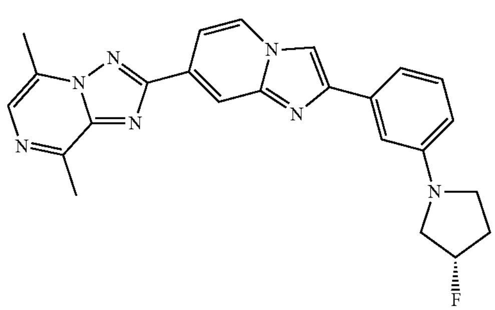 [SMILES: Cc1ncc(C)n2nc(-c3ccn4cc(-c5cccc(N6CC[C@H](F)C6)c5)nc4c3)nc12] | A | 0.16 |
| 29 | 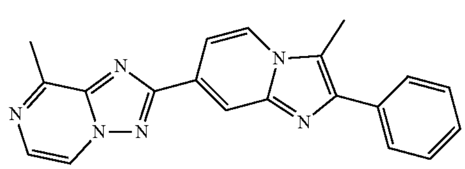 [SMILES: Cc1nccn2nc(-c3ccn4c(C)c(-c5ccccc5)nc4c3)nc12] | B | 2.4 |

TABLE 1-continued

| Example | Structure | PDE10 IC$_{50}$ (Range) | PDE10 IC$_{50}$ (nM) |
|---------|-----------|-------------------------|----------------------|
| 30 | 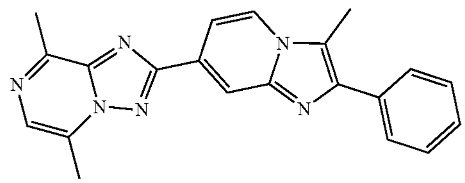 [SMILES: Cc1ncc(C)n2nc(-c3ccn4c(C)c(-c5ccccc5)nc4c3)nc12] | A | |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

(I)

or a pharmaceutically acceptable salt thereof, wherein
R$^x$ is selected from C$_3$-C$_5$ cycloalkyl and wherein * denotes the point of attachment to the parent molecule;
Q is selected from N and CR$^1$;
Q$^1$ is selected from N and CR$^4$;
R$^1$-R$^5$ are independently selected from hydrogen, C$_1$-C$_6$ alkoxy, C$_1$-C$_6$ alkyl, cyano, C$_3$-C$_5$ cycloalkyl, halo, and pyrrolidinyl;
R$^6$ is selected from hydrogen and C$_1$-C$_6$ alkyl;
X is selected from N and CR$^7$;
one of R$^7$ and R$^8$ is selected from hydrogen, cyano, halo, and pyrrolidinyl optionally substituted with one halogen; and the other is a heteroaromatic group of formula (II)

(II)

wherein the heteroaromatic group may be optionally substituted with one, two, or three substituents independently selected from C$_1$-C$_6$ alkoxy; C$_1$-C$_6$ alkyl; aryl; cyano; halo; halo(C$_1$-C$_6$)alkyl; and C$_1$-C$_6$ hydroxyalkyl; and
wherein * denotes the point of attachment to the parent molecule;
provided that when X is N, R$^8$ is the heteroaromatic group of formula (II).

2. A compound of claim 1, or a pharmaceutically acceptable salt thereof, wherein X is CR$^7$.

3. A compound of claim 2, or a pharmaceutically acceptable salt thereof, wherein R$^7$ is selected from hydrogen, cyano, and halo and pyrrolidinyl optionally substituted with one halogen.

4. A compound of claim 1, or a pharmaceutically acceptable salt thereof, wherein R$^8$ is

;

wherein * denotes the point of attachment to the parent molecule.

5. A compound of formula (I')

(I')

or a pharmaceutically acceptable salt thereof, wherein
X is selected from N and CR⁷;
R¹-R⁵ are independently selected from hydrogen, $C_1$-$C_6$ alkoxy, $C_1$-$C_6$ alkyl, cyano, and halo;
R⁶ is selected from hydrogen and $C_1$-$C_6$ alkyl;
one of R⁷ and R⁸ is selected from hydrogen, cyano, and halo and the other is a heteroaromatic group of formula (II)

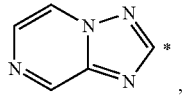

(II)

wherein the heteroaromatic group may be optionally substituted with one, two, or three substituents independently selected from $C_1$-$C_6$ alkoxy; $C_1$-$C_6$ alkyl; aryl; cyano; halo; halo($C_1$-$C_6$)alkyl; and $C_1$-$C_6$ hydroxyalkyl; and wherein * denotes the point of attachment to the parent molecule;

provided that when X is N, R⁸ is the heteroaromatic group of formula (II).

6. A compound selected from:
5,8-dimethyl-2-(2-phenylimidazo[1,2-a]pyridin-7-yl)-[1,2,4]triazolo[1,5-a]pyrazine;
2-(2-(3-chlorophenyl)imidazo[1,2-a]pyridin-7-yl)-5,8-dimethyl-[1,2,4]triazolo[1,5-a]pyrazine;
2-(2-(2-methoxyphenyl)imidazo[1,2-a]pyridin-7-yl)-5,8-dimethyl-[1,2,4]triazolo[1,5-a]pyrazine;
2-(2-(2,5-dichlorophenyl)imidazo[1,2-a]pyridin-7-yl)-5,8-dimethyl-[1,2,4]triazolo[1,5-a]pyrazine;
2-(2-(4-chlorophenyl)imidazo[1,2-a]pyridin-7-yl)-5,8'-dimethyl-[1,2,4]triazolo[1,5-a]pyrazine;
2-(2-(2,4-dimethylphenyl)imidazo[1,2-a]pyridin-7-yl)-5,8-dimethyl-[1,2,4]triazolo[1,5-a]pyrazine;
3-(7-(5,8-dimethyl-[1,2,4]triazolo[1,5-a]pyrazin-2-yl)imidazo[1,2-a]pyridin-2-yl)benzonitrile;
2-(2-(4-fluorophenyl)imidazo[1,2-a]pyridin-7-yl)-5,8-dimethyl-[1,2,4]triazolo[1,5-a]pyrazine;
2-(2-(2,4-difluorophenyl)imidazo[1,2-a]pyridin-7-yl)-5,8-dimethyl-[1,2,4]triazolo[1,5-a]pyrazine;
2-(6-bromo-2-phenylimidazo[1,2-a]pyridin-7-yl)-5,8-dimethyl-[1,2,4]triazolo[1,5-a]pyrazine;
7-(5,8-dimethyl-[1,2,4]triazolo[1,5-a]pyrazin-2-yl)-2-phenylimidazo[1,2-a]pyridine-6-carbonitrile;
2-(2-(2-fluorophenyl)imidazo[1,2-a]pyridin-7-yl)-5,8-dimethyl-[1,2,4]triazolo[1,5-a]pyrazine;
5,8-dimethyl-2-(2-(pyridin-2-yl)imidazo[1,2-a]pyridin-7-yl)-[1,2,4]triazolo[1,5-a]pyrazine;
2-(2-(3-fluorophenyl)imidazo[1,2-a]pyridin-7-yl)-5,8-dimethyl-[1,2,4]triazolo[1,5-a]pyrazine;
4-(7-(5,8-dimethyl-[1,2,4]triazolo[1,5-a]pyrazin-2-yl)imidazo[1,2-a]pyridin-2-yl)benzonitrile;
5,8-dimethyl-2-(2-phenyl-6-(pyrrolidin-1-yl)imidazo[1,2-a]pyridin-7-yl)-[1,2,4]triazolo[1,5-a]pyrazine;
5,8-dimethyl-2-(2-phenylimidazo[1,2-c]pyrimidin-7-yl)-[1,2,4]triazolo[1,5-a]pyrazine;
8-methyl-2-(2-phenylimidazo[1,2-a]pyridin-7-yl)-[1,2,4]triazolo[1,5-a]pyrazine;
8-methyl-2-(2-(pyridin-2-yl)imidazo[1,2-a]pyridin-7-yl)-[1,2,4]triazolo[1,5-a]pyrazine;
2-(2-cyclopropylimidazo[1,2-a]pyridin-7-yl)-5,8-dimethyl-[1,2,4]triazolo[1,5-a]pyrazine;
5,8-dimethyl-2-(2-(pyrazin-2-yl)imidazo[1,2-a]pyridin-7-yl)-[1,2,4]triazolo[1,5-a]pyrazine;
2-(2-(3-bromophenyl)imidazo[1,2-a]pyridin-7-yl)-8-methyl-[1,2,4]triazolo[1,5-a]pyrazine;
2-(2-(3-cyclopropylphenyl)imidazo[1,2-a]pyridin-7-yl)-8-methyl-[1,2,4]triazolo[1,5-a]pyrazine;
2-(2-(3-bromophenyl)imidazo[1,2-a]pyridin-7-yl)-5,8-dimethyl-[1,2,4]triazolo[1,5-a]pyrazine;
2-(2-(3-cyclopropylphenyl)imidazo[1,2-a]pyridin-7-yl)-5,8-dimethyl-[1,2,4]triazolo[1,5-a]pyrazine;
5,8-dimethyl-2-(2-(3-(pyrrolidin-1-yl)phenyl)imidazo[1,2-a]pyridin-7-yl)-[1,2,4]triazolo[1,5-a]pyrazine;
(S)-2-(2-(3-(3-fluoropyrrolidin-1-yl)phenyl)imidazo[1,2-a]pyridin-7-yl)-5,8-dimethyl-[1,2,4]triazolo[1,5-a]pyrazine;
8-methyl-2-(3-methyl-2-phenylimidazo[1,2-a]pyridin-7-yl)-[1,2,4]triazolo[1,5-a]pyrazine; and
5,8-dimethyl-2-(3-methyl-2-phenylimidazo[1,2-a]pyridin-7-yl)-[1,2,4]triazolo[1,5-a]pyrazine;
or a pharmaceutically acceptable salt thereof.

7. A composition comprising a compound of claim 1, or a pharmaceutically acceptable salt thereof, and a pharmaceutically acceptable carrier.

8. A method of treating schizophrenia in a patient, comprising administering to the patient a therapeutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 8,975,276 B2  
APPLICATION NO. : 13/531840  
DATED : March 10, 2015  
INVENTOR(S) : Schmitz et al.

Page 1 of 1

It is certified that error appears in the above-identified patent and that said Letters Patent is hereby corrected as shown below:

In the Claims:

Claim 1, col. 50, line 17, delete "formula (II)" and insert -- formula (II): --, Claim 5, delete " 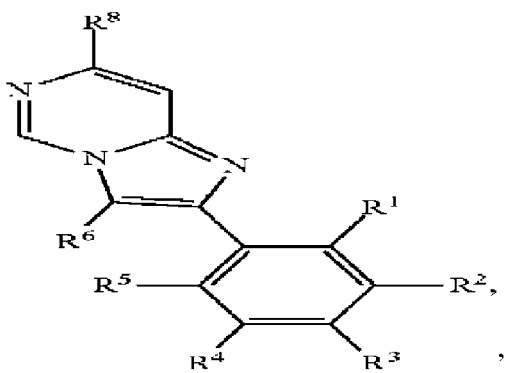 " and insert -- 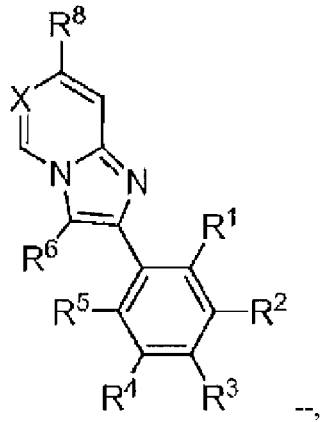 --, Claim 5, col. 51, line 11, delete "formula (II)" and insert -- formula (II): --, Claim 6, col. 51, line 38, delete "8'-dimethyl-" and insert -- 8-dimethyl- --.

Signed and Sealed this  
Nineteenth Day of January, 2016

Michelle K. Lee  
*Director of the United States Patent and Trademark Office*